(12) United States Patent
Jackson

(10) Patent No.: US 11,707,301 B2
(45) Date of Patent: Jul. 25, 2023

(54) THREADED CLOSURE FOR BONE ANCHOR RECEIVERS WITH PARALLEL PLANAR OUTER SURFACES AND METHODS OF USE

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 17/934,262

(22) Filed: Sep. 22, 2022

(65) Prior Publication Data

US 2023/0016980 A1 Jan. 19, 2023

Related U.S. Application Data

(63) Continuation of application No. 16/987,741, filed on Aug. 7, 2020, now Pat. No. 11,523,847, which is a continuation of application No. 16/005,873, filed on Jun. 12, 2018, now Pat. No. 10,751,095, which is a continuation of application No. 15/867,095, filed on Jan. 10, 2018, now Pat. No. 9,999,452, which is a continuation of application No. 14/043,139, filed on Oct. 1, 2013, now Pat. No. 10,039,577, which is a continuation of application No. 12/583,821, filed on Aug. 26, 2009, now Pat. No. 8,591,515, which is a continuation of application No. 10/996,349, filed on Nov. 23, 2004, now Pat. No. 7,621,918.

(51) Int. Cl.
*A61B 17/70* (2006.01)

(52) U.S. Cl.
CPC ...... *A61B 17/7037* (2013.01); *A61B 17/7002* (2013.01); *A61B 17/7082* (2013.01); *A61B 17/7085* (2013.01); *A61B 17/7091* (2013.01); *A61B 17/7011* (2013.01); *A61B 17/7032* (2013.01)

(58) Field of Classification Search
CPC .................................. A61B 17/7032–17/704
See application file for complete search history.

(56) References Cited

U.S. PATENT DOCUMENTS

| | | | | |
|---|---|---|---|---|
| 2002/0133154 A1* | 9/2002 | Saint Martin | ...... | A61B 17/7037 606/264 |
| 2004/0049196 A1* | 3/2004 | Jackson | ................ | F16B 35/047 606/916 |
| 2005/0216000 A1* | 9/2005 | Colleran | ............ | A61B 17/7037 606/328 |

\* cited by examiner

*Primary Examiner* — Julianna N Harvey
(74) *Attorney, Agent, or Firm* — Polsinelli PC

(57) ABSTRACT

A method for securing an elongate rod to a bone anchor with a receiver and a threaded plug. The receiver includes a channel configured to receive the elongate rod, and a helically wound receiver guide and advancement structure formed into the interior surfaces of the receiver. The threaded plug is configured for positioning within the channel to secure the elongate rod to the receiver in a locked configuration, with the threaded plug having an outer surface with a mating continuous helically wound guide and advancement structure configured for rotatable engagement with the receiver guide and advancement structure.

13 Claims, 30 Drawing Sheets

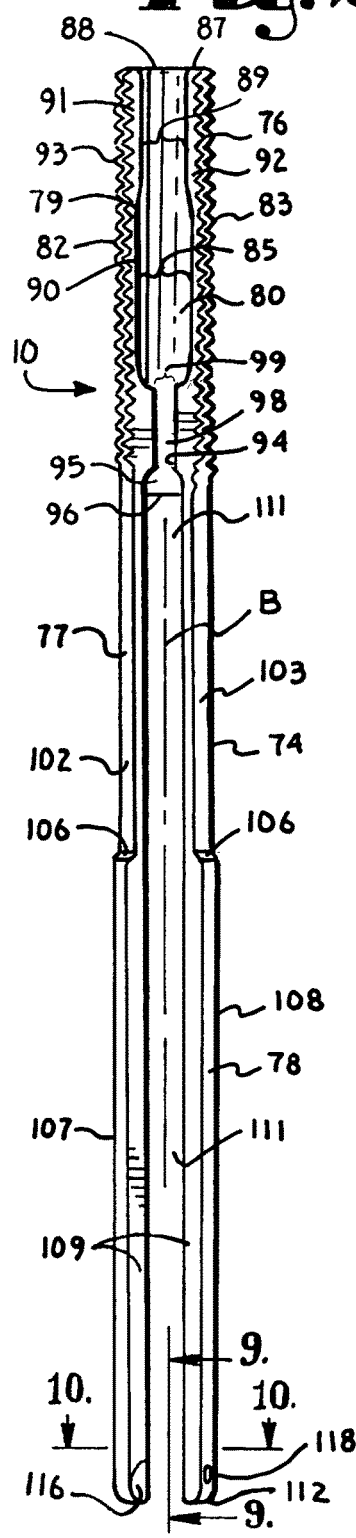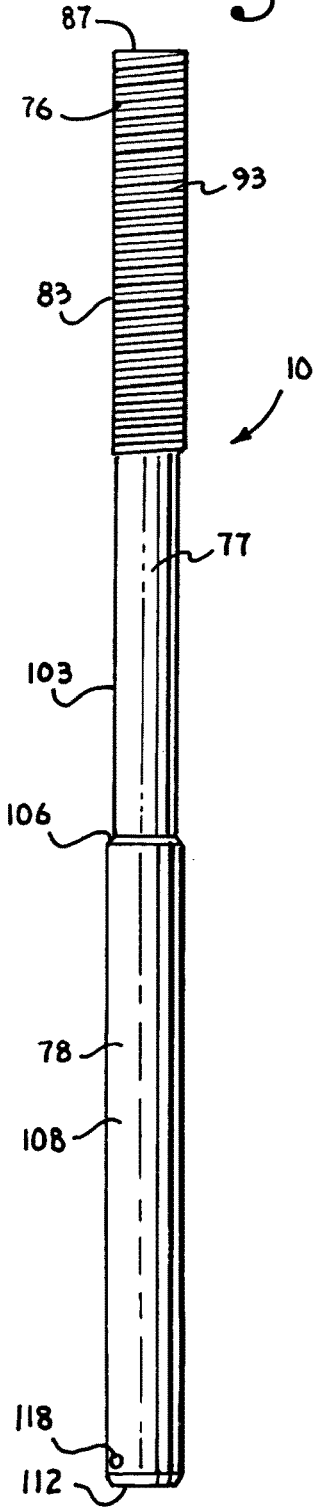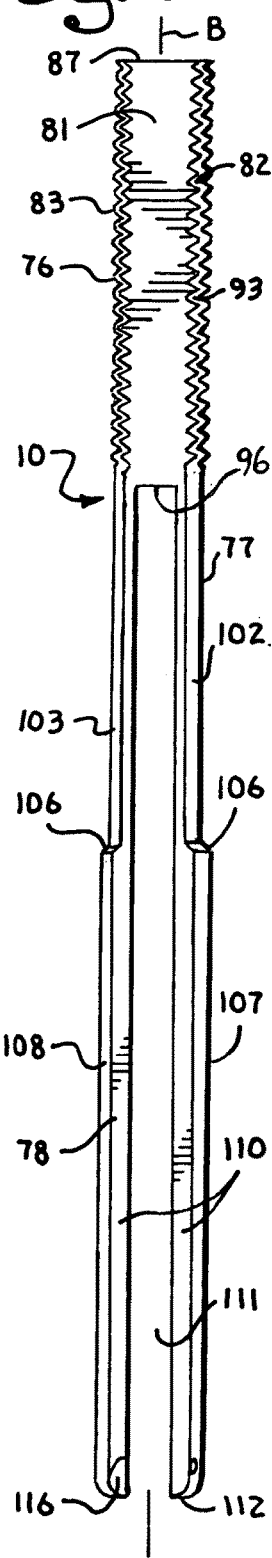

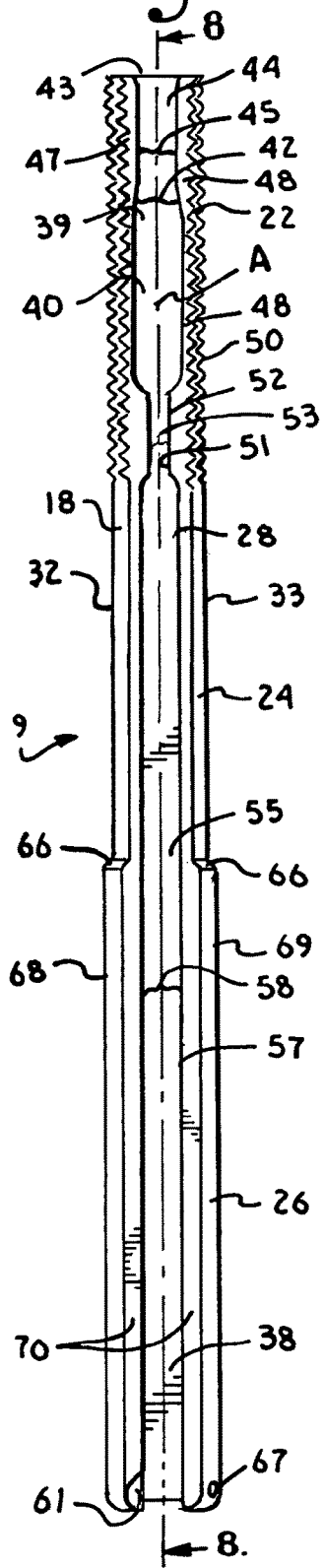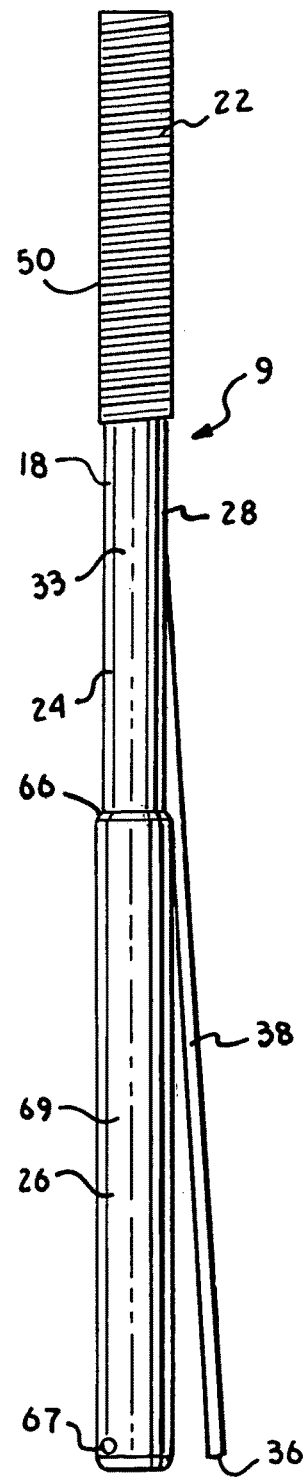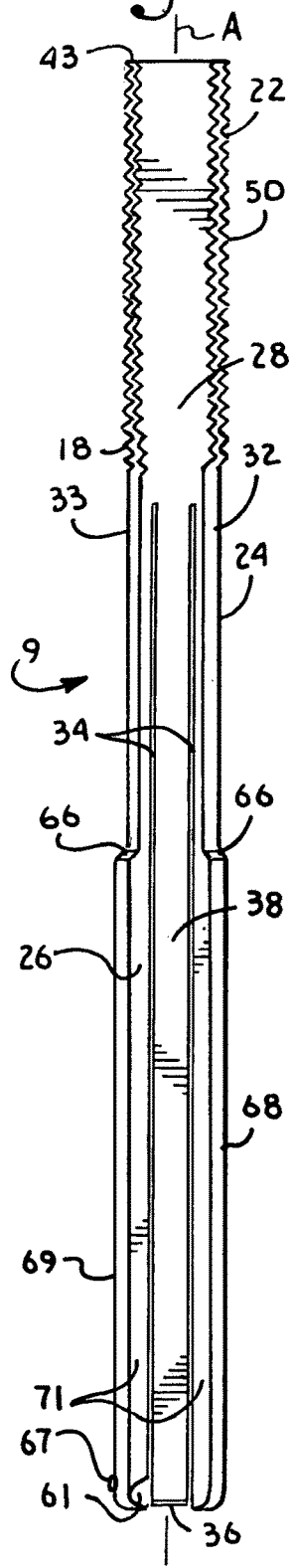

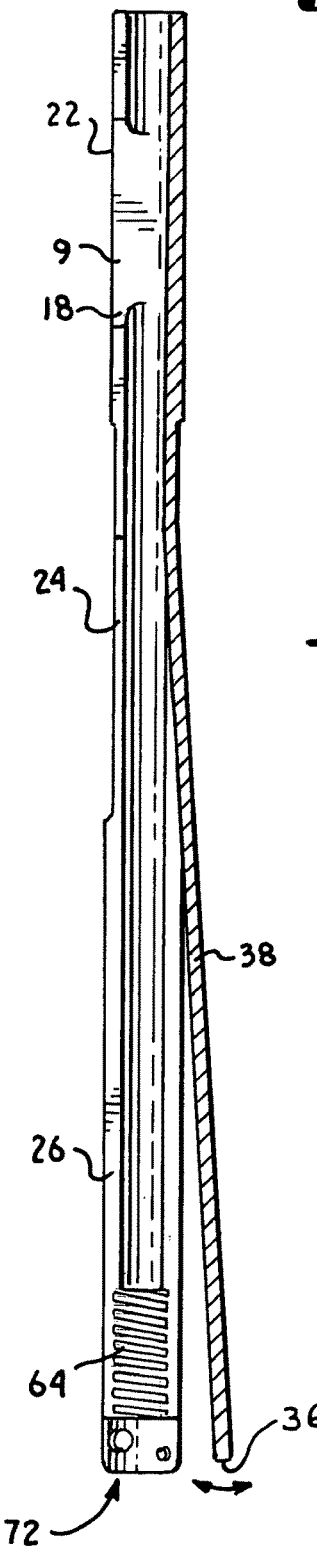
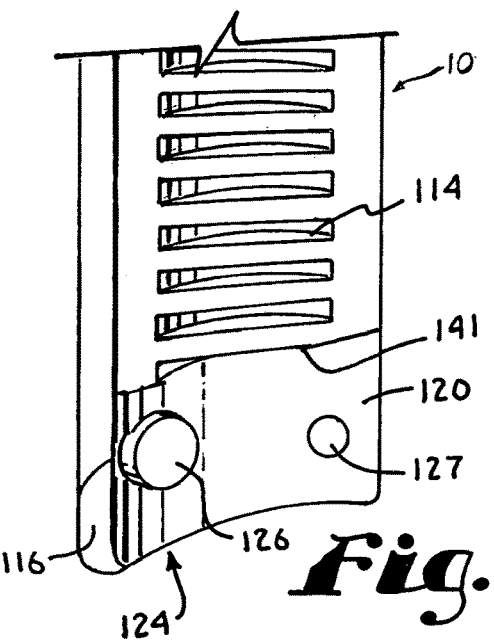
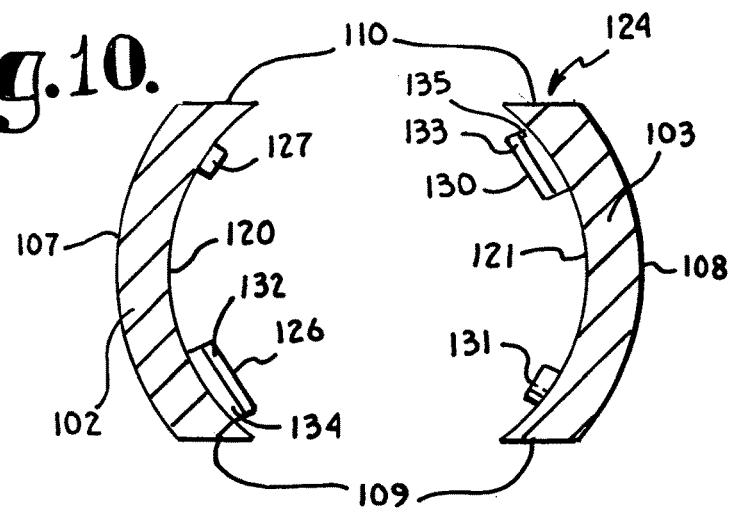
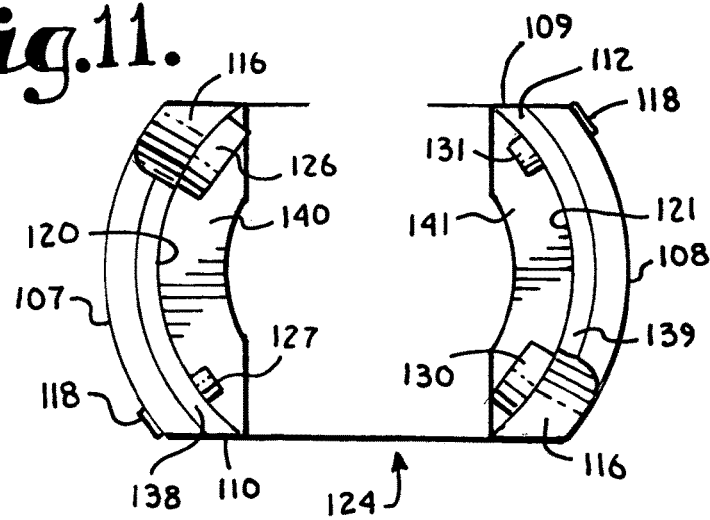

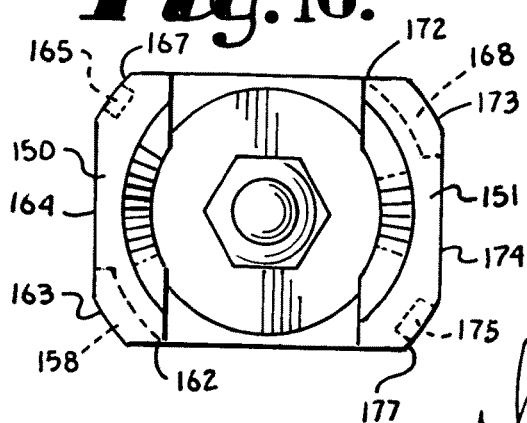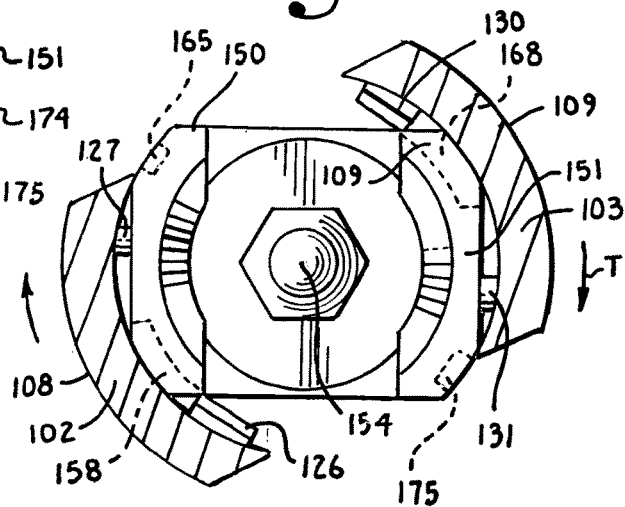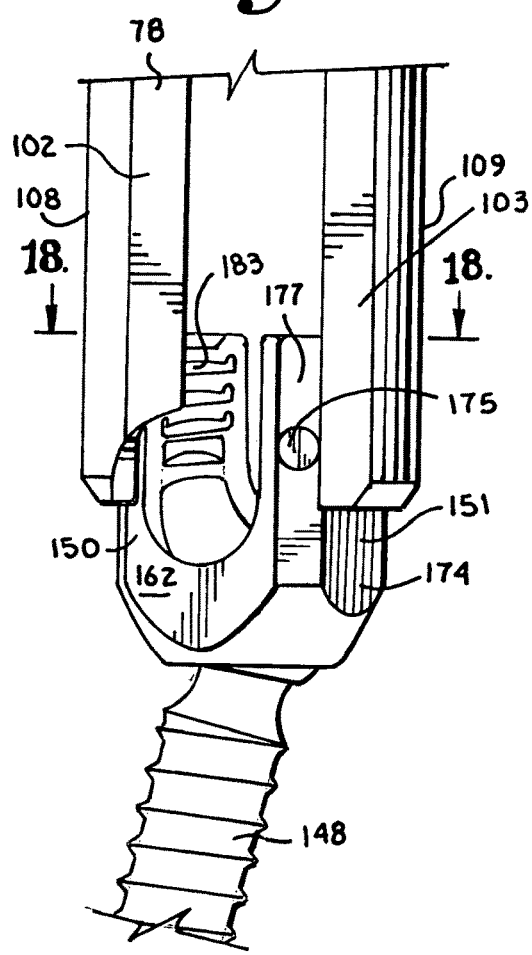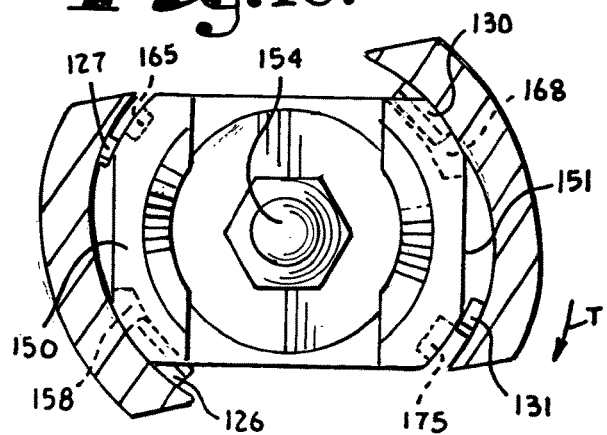

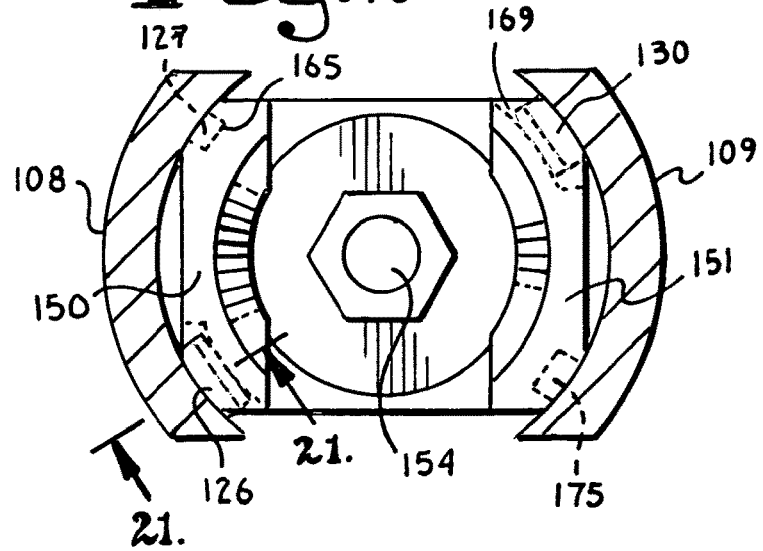
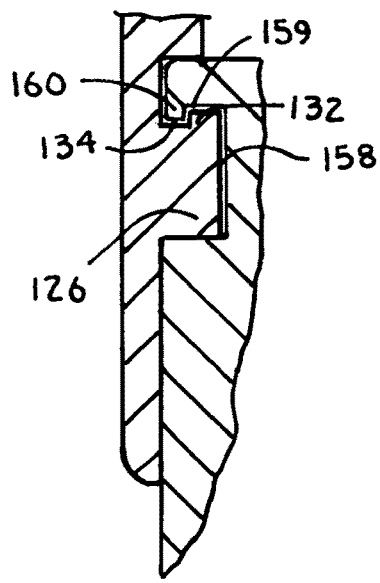
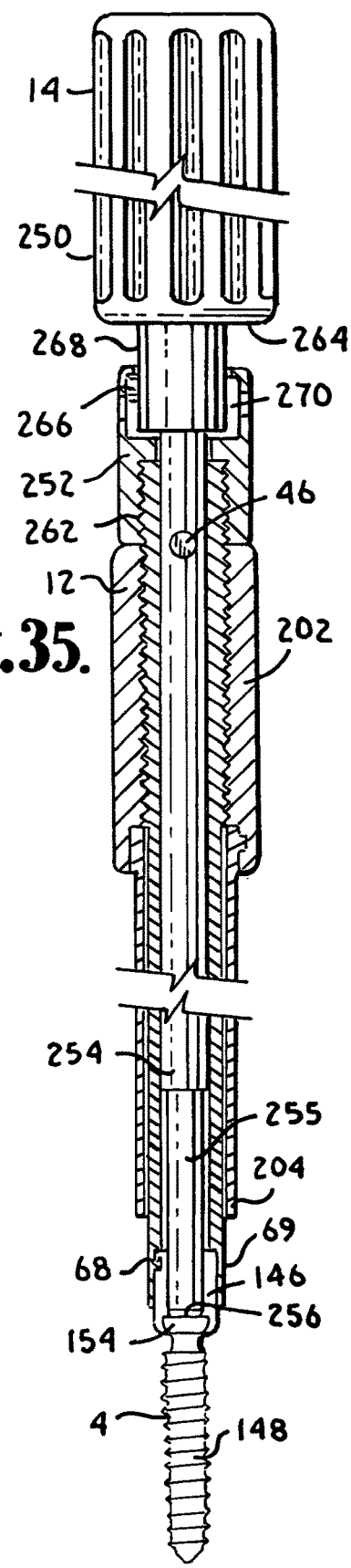

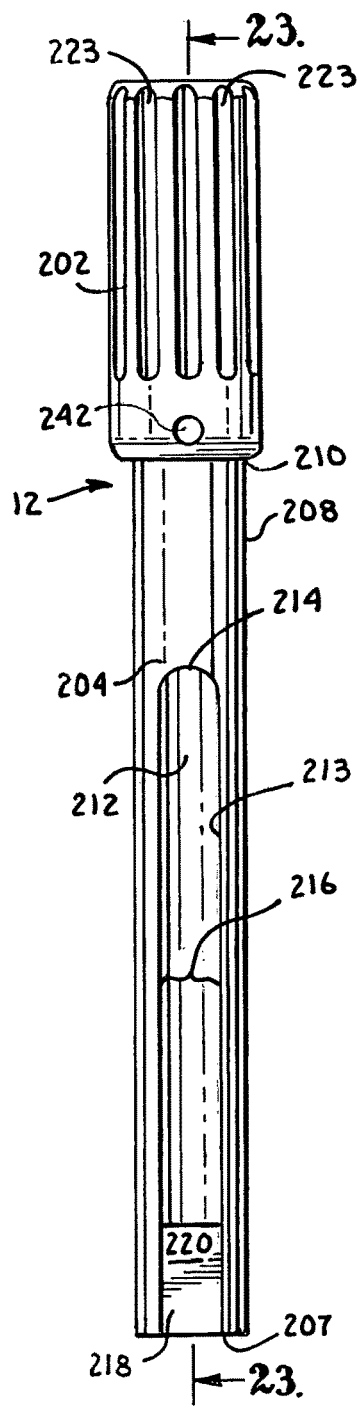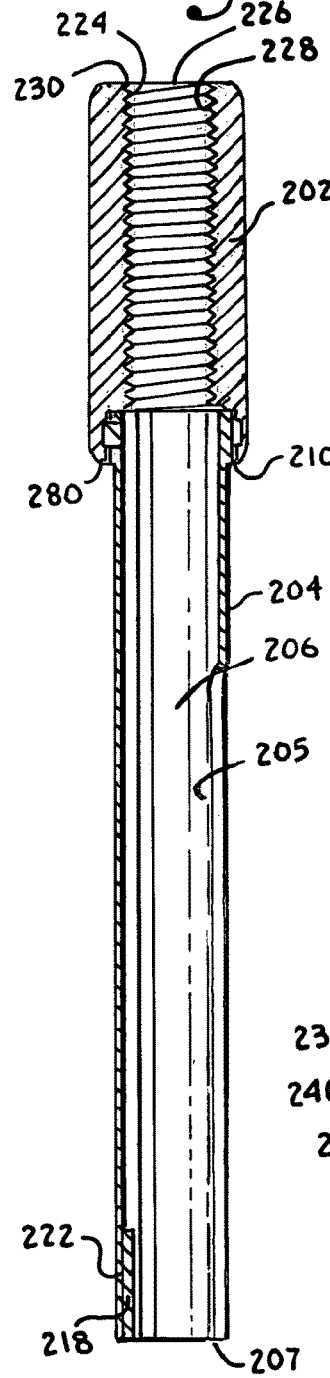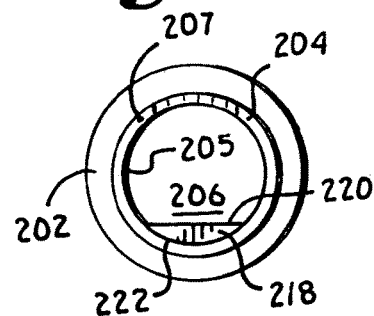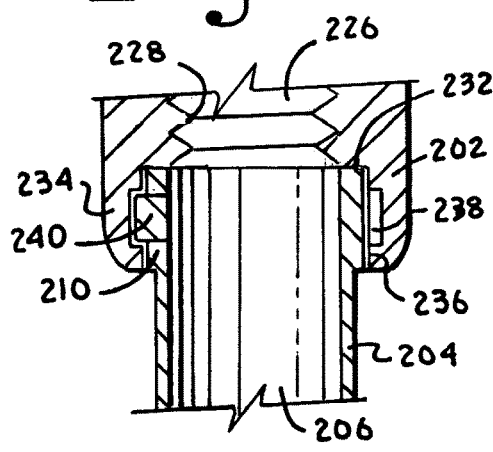

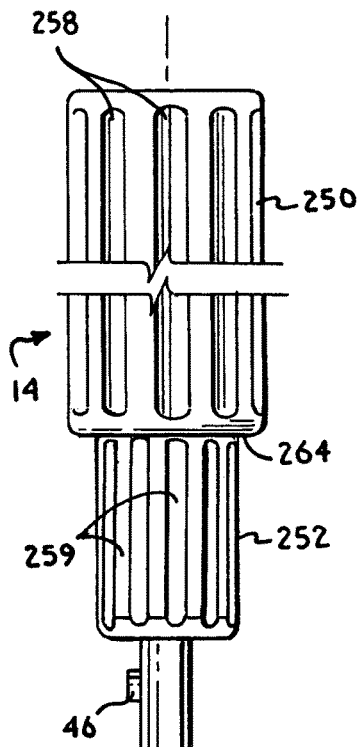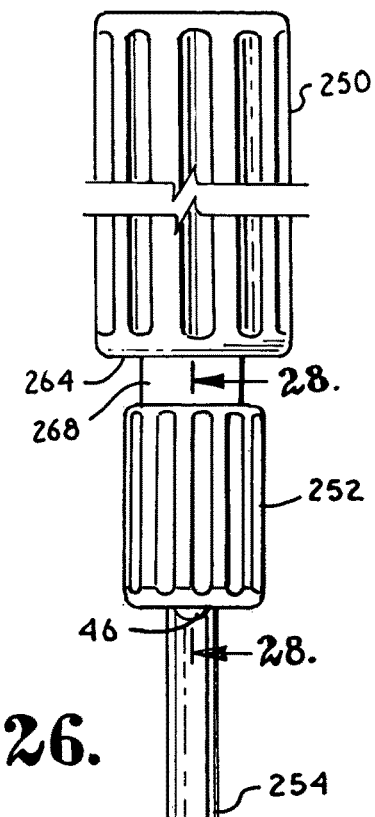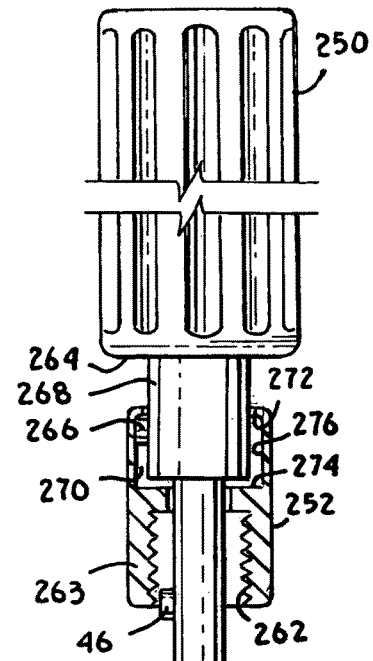

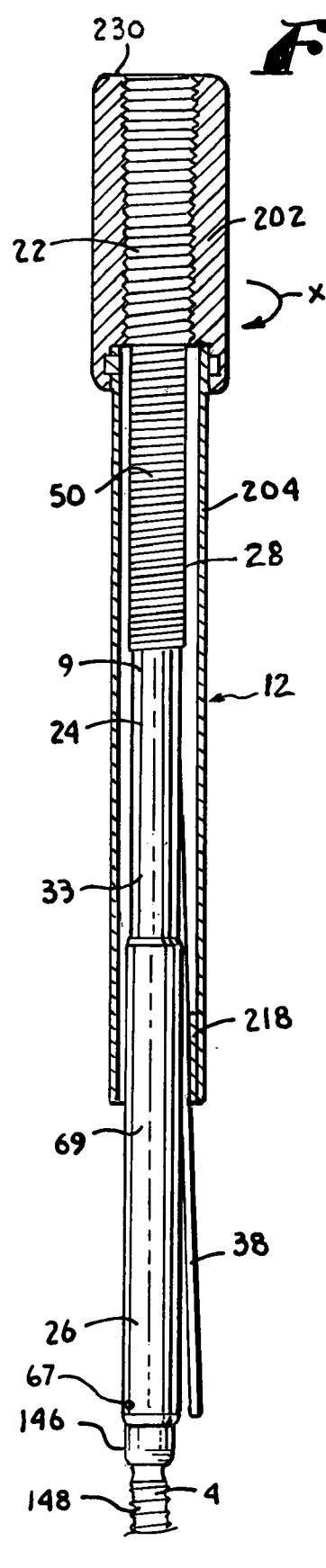
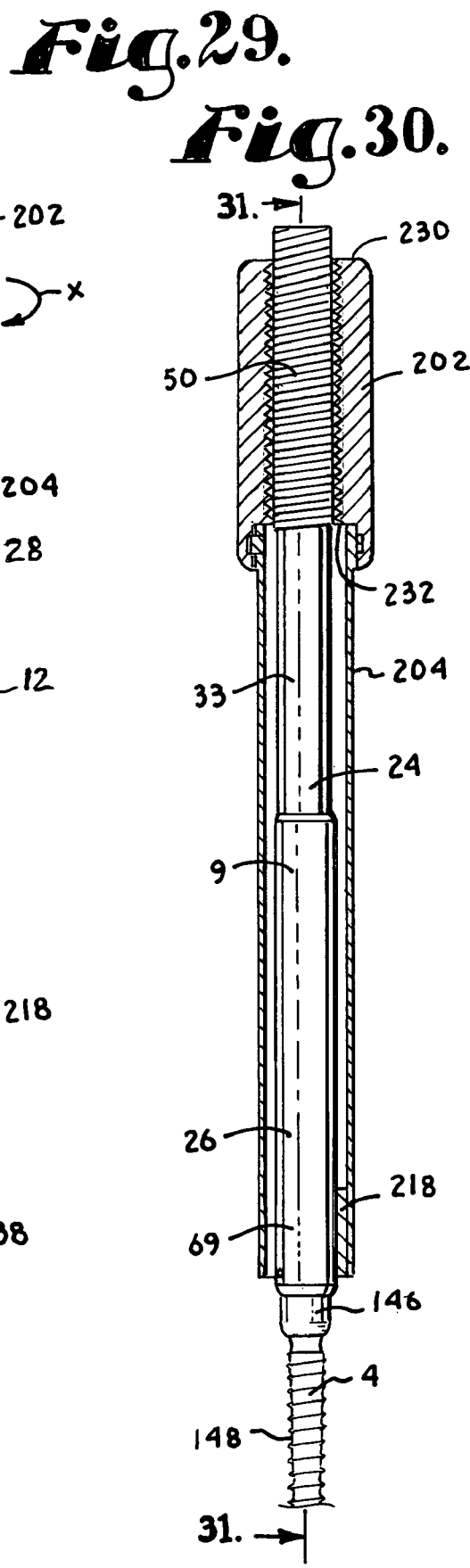
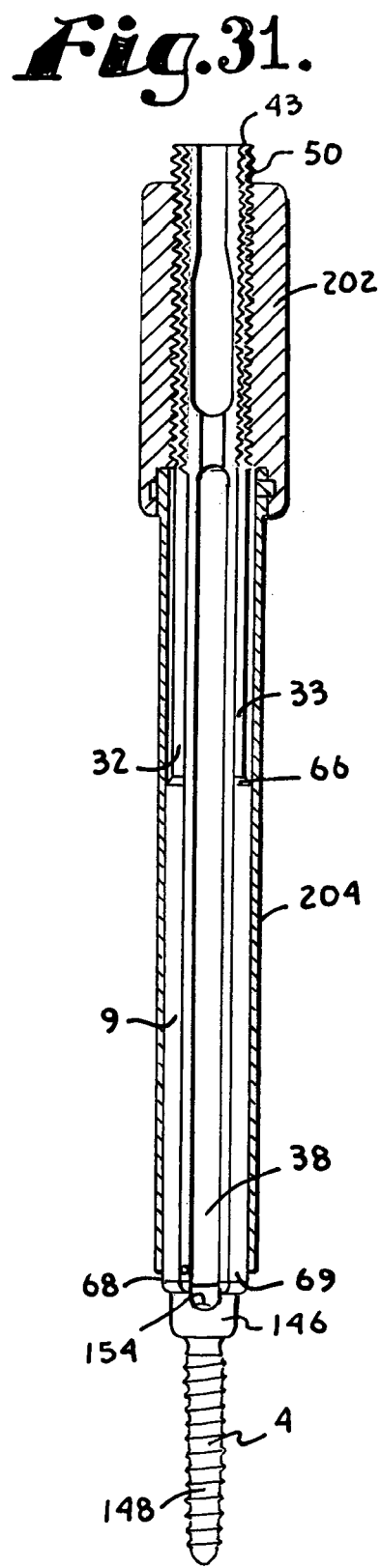
Fig.29.
Fig.30.
Fig.31.

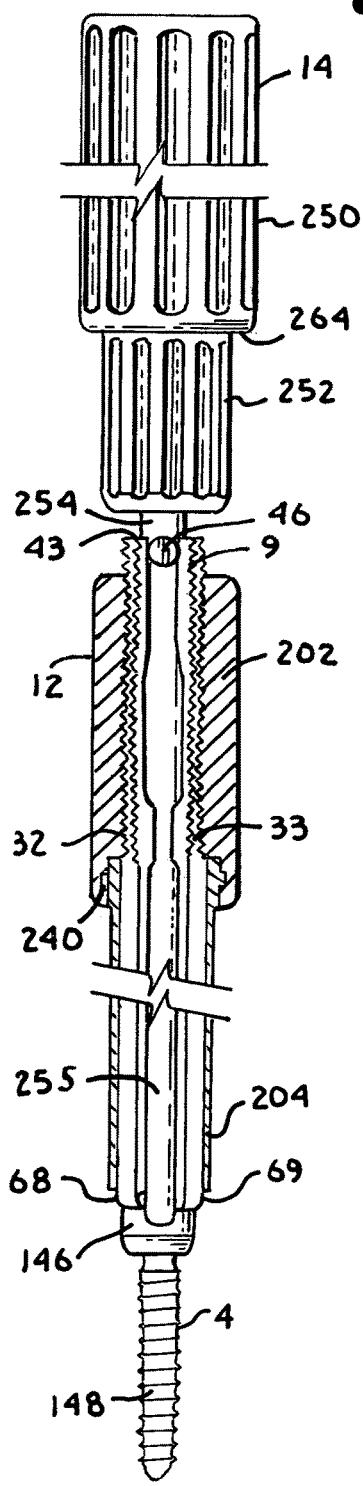
Fig.32.
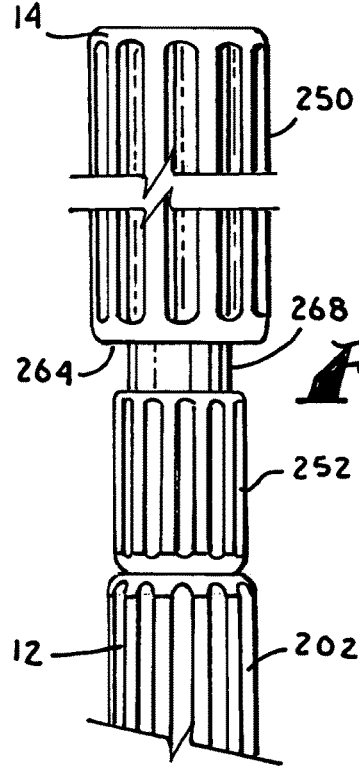
Fig.33.
Fig.34.

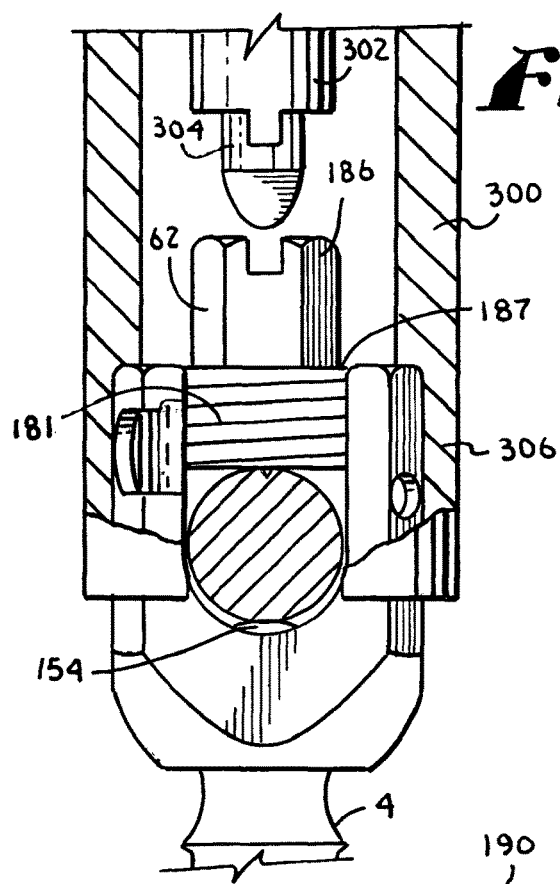
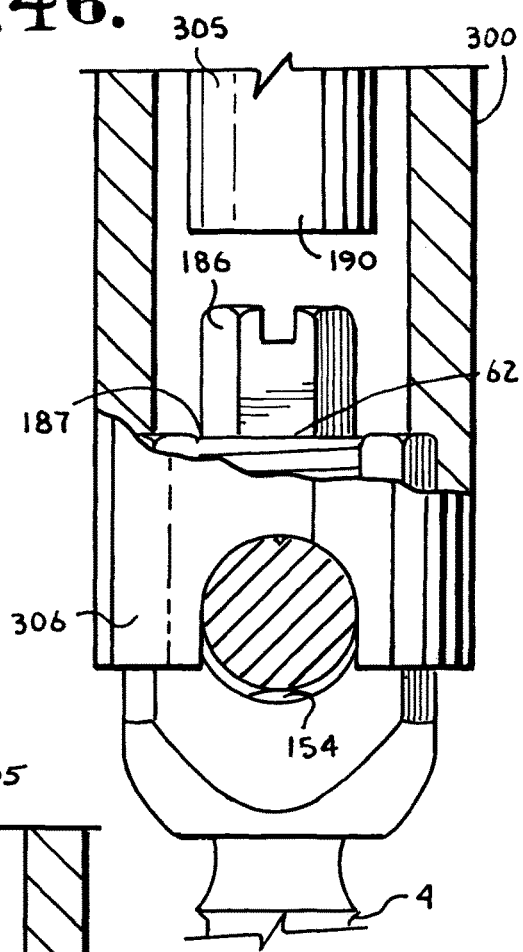
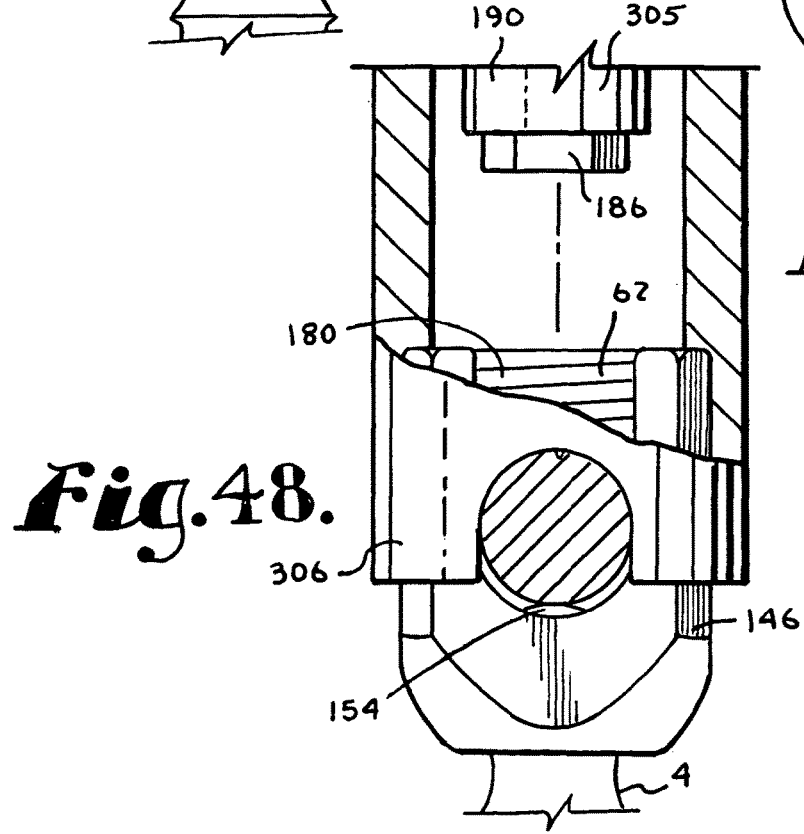
Fig.46.
Fig.47.
Fig.48.

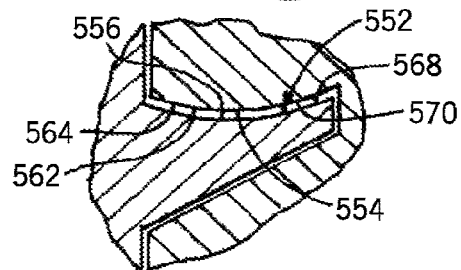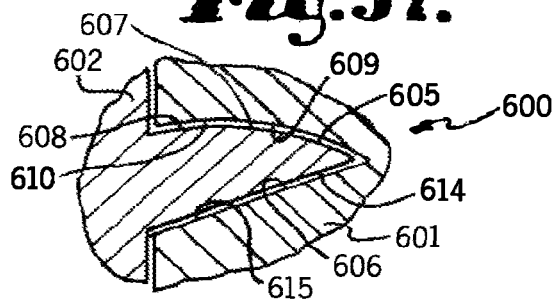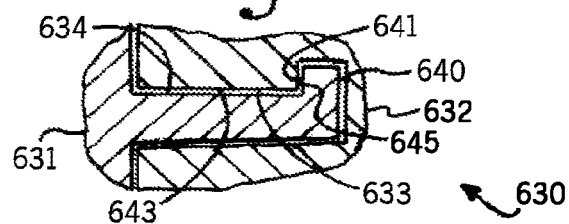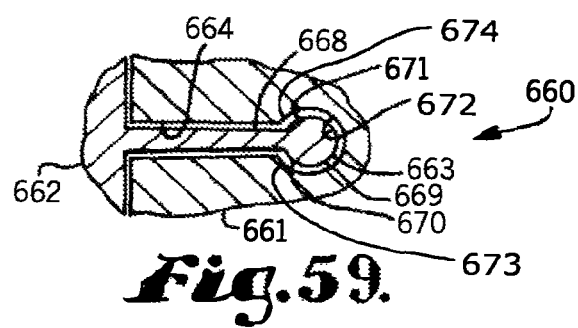

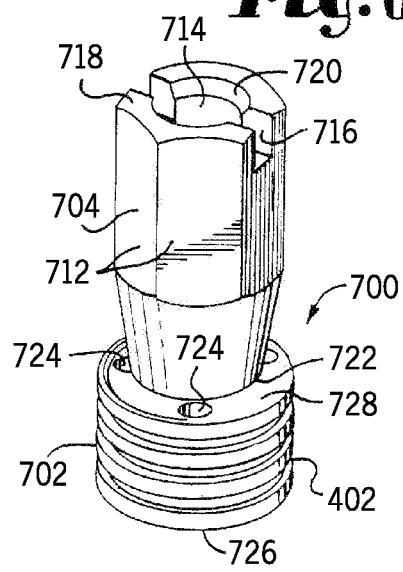
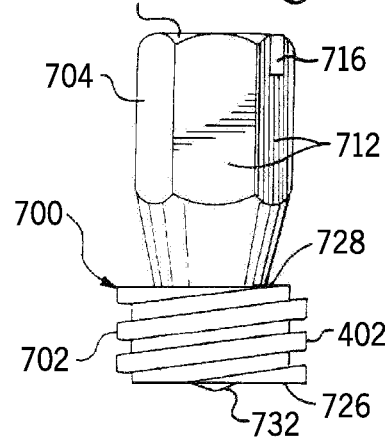
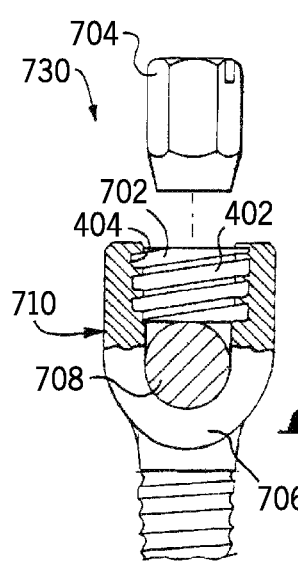

THREADED CLOSURE FOR BONE ANCHOR RECEIVERS WITH PARALLEL PLANAR OUTER SURFACES AND METHODS OF USE

CROSS REFERENCE TO RELATED APPLICATIONS

This application is a continuation of U.S. patent application Ser. No. 16/987,741, filed Aug. 7, 2020, which is a continuation of U.S. patent application Ser. No. 16/005,873, filed Jun. 12, 2018, now U.S. Pat. No. 10,751,095, which is a continuation of U.S. patent application Ser. No. 15/867,095, filed Jan. 10, 2018, now U.S. Pat. No. 9,999,452, which is a continuation of U.S. patent application Ser. No. 14/043,139, filed Oct. 1, 2013, now U.S. Pat. No. 10,039,577, which is a continuation of U.S. patent application Ser. No. 12/583,821, filed Aug. 26, 2009, now U.S. Pat. No. 8,591,515, which is a continuation of U.S. patent application Ser. No. 10/996,349, filed Nov. 23, 2004, now U.S. Pat. No. 7,621,918, each of which is incorporated by reference in its entirety herein, and for all purposes.

BACKGROUND OF THE INVENTION

The present invention relates to apparatuses and methods for use in performing spinal surgery and, in particular, to tools and methods of using such tools, especially for percutaneously implanting spinal screws and for implanting a rod for spinal support and alignment, using minimally invasive techniques.

For many years, spinal osteosynthesis apparatuses have been utilized to correct spinal deformities, injuries or disease. In such procedures, elongate rods are surgically attached to vertebrae of the spine to provide support and/or to realign or reposition certain vertebrae. Such rods are secured to vertebrae utilizing bone screws and other spinal implants. In order to reduce the impact of such surgery on the patient, a desirable approach is to insert such implants percutaneously or with surgical techniques that are minimally invasive to the body of the patient.

Problems arise when implantation tools designed for traditional surgery that is highly invasive are utilized in percutaneous surgery. The tools may be bulky, oversized or have irregular surfaces or protrusions. A projecting actuator arm or fastening member may be useful with respect to the spinal screw implantation process or the rod reduction process, but there is insufficient clearance to use such structure and/or such structure may produce additional invasive trauma which the percutaneous surgery is attempting to avoid.

A percutaneous procedure also presents a problem with implantation of rods that are elongate and have historically required a long incision and open wound in order to provide for the length of the rod and the space required for the surgeon's hands to manipulate the rod. Such problems are then compounded by the implants and insertion tools used with the rod.

Consequently, it is desirable to develop apparatuses and techniques that allow for the insertion of bone screws, the insertion and reduction of a rod into the bone screws and the securing of the rod to the bone screws with significantly less invasion into the body of the patient and with minimal surgical incision of the skin over the operational site.

SUMMARY OF THE INVENTION

A tool assembly and a set of tools according to the invention is provided for percutaneously implanting bone screws and an associated spinal rod in a patient. The tool assembly includes an elongate guide tool with implant engaging members and a multi-purpose installation tool. The multi-purpose tool is a stabilizer for the guide tool implant engaging members which also functions as a rod stabilizer tang container and deployer and a rod pusher and reducer. The guide tool has a lower end configured with opposed implant engaging members for releaseable attachment to a spinal implant bone screw, hook, etc. The multi-purpose installation tool is elongate, and preferably includes a translation nut and attached sleeve which has a lower end for engaging and containing the rod stabilizer tang prior to rod insertion and later pushing on the rod for reduction. The translation nut is coaxial and freely rotatable with respect to the sleeve. The nut is configured for rotatable attachment to an upper end of the guide tool. The multi-purpose installation tool sleeve is attachable or securable to the guide tool in a first bone screw implantation orientation and in an alternative second rod pushing orientation. In the first, bone screw implantation orientation, the sleeve is disposed in a fixed, stationary position with respect to the guide tool, with the sleeve substantially surrounding the guide tool and retaining a flexible tang. In the second or rod pushing orientation, the sleeve is slidable along an axis of the guide tool and the nut can be rotated, thereby translating the rod pushing end between a first location substantially spaced from the guide tool end and a second location near the guide tool end for rod reduction.

The tool assembly may further include a driver having a handle, a guide tool attachment portion and a stem, the stem having an end configured for rotatable engagement with a spinal implant screw. The driver is in coaxial relationship with both the guide tool and the multi-purpose installation tool when the stem is disposed within the guide tool with the guide tool attached to the multi-purpose installation tool. The attachment portion of the driver is configured for rigid attachment to the guide tool, preventing rotation of the driver in relation to the guide tool.

A tool set according to the invention includes at least a pair of end guide tools. Each end guide tool includes an elongate body having opposed implant engaging members with lower attachment structure adapted for attachment to a respective bone screw. The body has an inner surface defining an elongate and laterally opening channel. Preferably, the guide tool body further defines an elongate opening communicating with the channel and a back wall with a flexible holding structure, the wall and holding structure disposed opposite the lateral opening. The back wall flexible holding structure includes first and second elongate and parallel slits in the lower back wall portion creating a movable tab or tang disposed between the first and second slits. The flexible flap or tang partially defines the elongate channel. Furthermore, during insertion procedures, the tang may be pushed so as to flex, hinge or spring at an upper end thereof and so that a lower end angulates and translates outwardly or to a location lateral relative to a remainder of the back wall, with the channel adapted to receive a respective rod therein. When an end of the rod is inserted in the lower end channel, the tang may be resiliently flexed further outwardly to accommodate the length of the rod while maintaining, containing and stabilizing the rod in a desired position relative to bone screws.

The multi-purpose installation tool is attachable to the end guide tool in a first, bone screw implantation configuration position and in an opposite second, rod pushing configuration or position. In the first position, an elongate slot or opening in the sleeve of the tool support is aligned with and fixed in adjacent relationship to the channel opening of the end guide tool, with the sleeve of the tool being held adjacent to the back wall portion and retaining the spring tang. In the second, rod pushing position, the end guide tool back wall portion and the tool sleeve opening are fixed in adjacent relationship with the back wall tang portion protrudeable into the tool sleeve opening.

An intermediate guide tool according to the invention includes an end with opposed first and second implant engaging legs defining a longitudinal pass-through opening, passageway or slot for receiving a rod therethrough. When attached to a multi-purpose installation tool in the first, bone screw implantation orientation, the tool sleeve is disposed in a fixed, stationary position substantially surrounding and supporting both the intermediate guide tool legs. In the second or rod pushing orientation, the sleeve is in sliding relation along an axis of the intermediate guide tool, with the sleeve and associated rod pushing end translatable along the first and second legs between a first location spaced from the intermediate guide tool end and a second location adjacent or near the guide tool end.

A vertebral support rod implantation kit according to the invention, adapted for use with a plurality of vertebrae, includes a plurality of polyaxial bone screws, each bone screw being adapted for implantation in one vertebra, each of the bone screws having an attachment structure. The kit also includes an elongate rod having first and second ends, the rod sized and shaped to extend between a pair of end bone screws of the plurality of bone screws. The kit further includes a plurality of closure tops with each closure top being sized and shaped to mate with a respective bone screw and capture or retain the elongate rod within a cavity or channel defined by the respective arms of the bone screw. Additionally, the kit includes a pair of end guide tools, and may include one or more intermediate guide tools, each guide tool being attachable to multi-purpose installation tools, as described herein and bone screw drivers, the drivers being configured to be rigidly attached to a respective end guide tool or intermediate guide tool.

In a method according to the invention, a spinal fixation tool assembly is assembled by first attaching a bone screw head of a spinal implant screw to a mating attachment structure disposed at a first end of an elongate guide tool implant engaging member, the guide tool defining a laterally opening channel and having a second attachment structure disposed at a second end thereof. The guide tool and attached spinal implant screw are then inserted into a multi-purpose installation tool, the tool having a translation nut and a sleeve. The nut is rotated in a first direction to mate the tool support with the second attachment structure on the guide tool and translate the sleeve to a location near the guide tool first end. Then, a driver is inserted into the guide tool channel, the driver having a handle and a spinal implant screw engagement end. The driver is attached to the guide tool at the second attachment structure with the driver engagement end engaging the spinal implant screw.

A method according to the invention may also include the steps of inserting the attached driver, multi-purpose installation tool, guide tool and spinal implant screw into an incision, especially a minimally invasive incision sized to snugly or closely receive the assembled tools and bone screw, and into contact with a vertebra, followed by turning the driver handle. By turning the handle, the driver, the associated tools and the spinal implant screw are rotated as one assemblage or unit, driving the spinal implant screw into the vertebra.

Further method steps according to the invention include detaching the drivers from the attached guide and multi-purpose installation tools and withdrawing the drivers from the incisions, followed by detaching the multi-purpose installation tools from the end guide tools and thereby deploying the end tangs. It may also be desirable to detach the multi-purpose installation tools from the intermediate guide tools, if any.

According to the invention, during rod insertion, a respective multi-purpose installation tool may be utilized for rod reduction and accordingly replaced on each end guide tool with the sleeve opening thereof aligned with the end guide tool flexible wall or tang to allow the tang to remain flexed outward. Then a rod first end may be inserted into an incision through which one of the end guide tools has been inserted, and then guided into a channel of an adjacent end or intermediate guide tool. The rod is then guided into and through all remaining channels with first and second ends of the rod each in contact with a flexible wall or deployed tang of a respective end guide tool with the tangs biasing against the rod ends, and with the rod extending through all associated guide tools. The multi-purpose installation tool sleeve is then utilized as a rod pusher by rotating the nut and sliding the closed end of the sleeve toward the lower guide tool end, the sleeve end contacting the rod and pushing the rod toward the bone screw.

The attachment structure for joining the guide tool to the bone screw includes radial mating projections and receivers or grooves that allow the guide tool to be twisted on and twisted from the head of the bone screw. For example, an external attachment on the bone screw head can have tapered undercut upper surfaces. It is foreseen that other attachment structure could be used such as clip-on/clip-off, clip-on/twist-off, snap-on/snap-off, snap-on/twist-off, spring-on/spring-off, spring-on/twist-off, set screws, etc. The attachment structure secures the guide tool to the bone screw during insertion of the screw into bone, but allows the tool to release from the bone screw for removal of the tool at the end of the procedure by rotation of the tool about a central axis thereof or by some other mechanism, as described herein.

OBJECTS AND ADVANTAGES OF THE INVENTION

Therefore, the objects of the present invention are: to provide a compact tool assembly for supporting and installing bone screws and other implants with minimal surgical invasion to the patient; to provide such an assembly wherein a tool providing support and stabilization for implant engaging members of the assembly during bone screw implantation may also be utilized for deployment of rod containment tangs and as a rod reducer; to further provide a set of tools for implanting a spinal rod for support or alignment along a human spine with minimal surgical invasion of the patient; to provide such a set of tools including a pair of end tool guides for slidably guiding opposed ends of the rod toward end bone screws attached to the end guide tools; to provide such a set of tools including intermediate guide tools for each intermediate bone screw that guide the rod in slots therethrough to respective bone screws; to provide such a set of tools including rod and closure top installation tools for assisting in securing the rod in the bone screws; to provide such a set of tools wherein the guide tools are easily attached to and disengaged from the bone screws; to provide such a set of tools wherein the guide tools, guide tool supports or stabilizers, tang containment and deployment tools, rod reduction tools, bone screw installation tools and closure top installation tools are all easily aligned, positioned, and engaged, if necessary, with respect to the bone screw and are disengaged from the bone screw and other tools in the installation assembly by manual manipulation of the surgeon; to provide a method of implanting a rod into bone screws within a patient with minimal surgical invasion of the patient; to provide such a method utilizing the previously described tools for percutaneous implantation of such a rod; and to provide such a set of tools and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is an enlarged front elevational view of an intermediate guide tool of the invention.

FIG. 3 is an enlarged side elevational view of the intermediate guide tool of FIG. 2.

FIG. 4 is an enlarged rear elevational view of the intermediate guide tool of FIG. 2.

FIG. 5 is an enlarged front elevational view of the end guide tool of FIG. 1.

FIG. 6 is an enlarged side elevational view of the end guide tool of FIG. 5.

FIG. 7 is an enlarged rear elevational view of the end guide tool of FIG. 5.

FIG. 8 is a cross-sectional view of the end guide tool, taken along the line 8-8 of FIG. 5.

FIG. 9 is an enlarged cross-sectional view of the intermediate guide tool, taken along the line 9-9 of FIG. 2.

FIG. 10 is an enlarged cross-sectional view of the intermediate guide tool, taken along the line 10-10 of FIG. 2.

FIG. 11 is an enlarged bottom plan view of the intermediate guide tool of FIG. 2.

FIG. 16 is an enlarged top plan view of the polyaxial bone screw of FIG. 12.

FIG. 17 is an enlarged and fragmentary front elevational view of the polyaxial bone screw of FIG. 12 and the intermediate guide tool of FIG. 2, shown at an early stage of a twist-on installation of the intermediate guide tool to the bone screw head.

FIG. 18 is an enlarged and fragmentary cross-sectional view of the intermediate guide tool and polyaxial bone screw installation, taken along the line 18-18 of FIG. 17.

FIG. 19 is an enlarged and fragmentary cross-sectional view similar to FIG. 18, showing a later stage of the twist-on installation of the intermediate guide tool to the bone screw head.

FIG. 20 is an enlarged and fragmentary cross-sectional view similar to FIGS. 18 and 19, showing the intermediate guide tool installed on the bone screw head.

FIG. 21 is an enlarged, fragmentary and cross-sectional view, taken along the line 21-21 of FIG. 20, showing the intermediate guide tool installed on the bone screw head.

FIG. 22 is an enlarged front elevational view of the multi-purpose tool shown in FIG. 1.

FIG. 23 is a cross-sectional view of the multi-purpose tool taken along the line 23-23 of FIG. 22.

FIG. 24 is an enlarged bottom plan view of the multi-purpose tool of FIG. 22.

FIG. 25 is an enlarged and fragmentary cross-sectional view of a portion of the multi-purpose tool shown in FIG. 23.

FIG. 26 is an enlarged and fragmentary side elevational view of the driver shown in FIG. 1 having a handle, a nut fastener and a stem, with the nut fastener being shown in a first, unengaged position.

FIG. 27 is an enlarged and fragmentary front elevational view of the driver tool similar to FIG. 26, showing the nut fastener in a second or intermediate position.

FIG. 28 is an enlarged and fragmentary side elevational view similar to FIG. 27 and further showing a cross-sectional view of the nut fastener, taken along the line 28-28 of FIG. 27.

FIG. 29 is an enlarged cross-sectional view similar to FIG. 23, showing an early stage of the installation of the multi-purpose tool to the end guide tool (shown in side elevation as in FIG. 6).

FIG. 30 is an enlarged cross-sectional view similar to FIG. 29, showing the multi-purpose tool installed to the end guide tool (shown in side elevation).

FIG. 31 is an enlarged cross-sectional view of the multi-purpose tool, taken along the line 31-31 of FIG. 30, showing the end guide tool in front elevation.

FIG. 32 is an enlarged and fragmentary cross-sectional view of the multi-purpose tool similar to FIG. 31, shown attached to the end guide tool and also showing a sliding engagement stage of attachment to the driver (shown in front elevation).

FIG. 33 is an enlarged and fragmentary front elevational view similar to FIG. 32, showing the driver nut fastener in the intermediate position shown in FIG. 27.

FIG. 34 is an enlarged and fragmentary front elevational view similar to FIG. 33, showing the driver in fixed engagement with the guide tool.

FIG. 35 is an enlarged and fragmentary view similar to FIG. 34, showing the driver in fixed engagement with the guide tool and with the driver nut fastener shown in cross-section as in FIG. 28, and the multi-purpose tool shown in cross-section as in FIG. 32.

FIG. 46 is a fragmentary and front elevational view of a bone screw with attached break-away closure member and installed rod, and further showing the closure top installation tool of FIG. 44 with the anti-torque tool.

FIG. 47 is a fragmentary and front elevational view of a bone screw and anti-torque tool with portions broken away to show a torque driver advancing toward the break-away closure member in a process according to the invention.

FIG. 48 is a fragmentary and front elevational view of the bone screw and anti-torque tool similar to FIG. 47, with portions broken away to show a fully installed rod and closure member with the break-away head removed from the top by the torque driver.

FIG. 56 is a fragmentary cross sectional view of a seventh modified bone screw and closure, similar to the embodiment in FIG. 55, showing a pair of interlocking forms in accordance with the present invention.

FIG. 57 is a fragmentary cross sectional view of an eighth modified embodiment of a bone screw and closure showing a pair of interlocking forms in accordance with the invention.

FIG. 58 is a fragmentary cross sectional view of an ninth modified embodiment of a bone screw and closure showing a pair of interlocking forms in accordance with the invention.

FIG. 59 is a fragmentary cross sectional view of an tenth modified embodiment of a bone screw and closure showing a pair of interlocking forms in accordance with the invention.

FIG. 60 is a perspective view of an example closure for an open headed bone screw that has a helical wound gripping interlocking form in accordance with the present invention mounted thereon.

FIG. 61 is a side elevational view of the closure.

FIG. 62 is a side elevational view illustrating an interlocking form of the closure mated with and installed in a companion interlocking form on an open headed bone screw to capture a fixation rod within a head of the bone screw and with the head of the bone screw partially broken away to illustrate detail thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
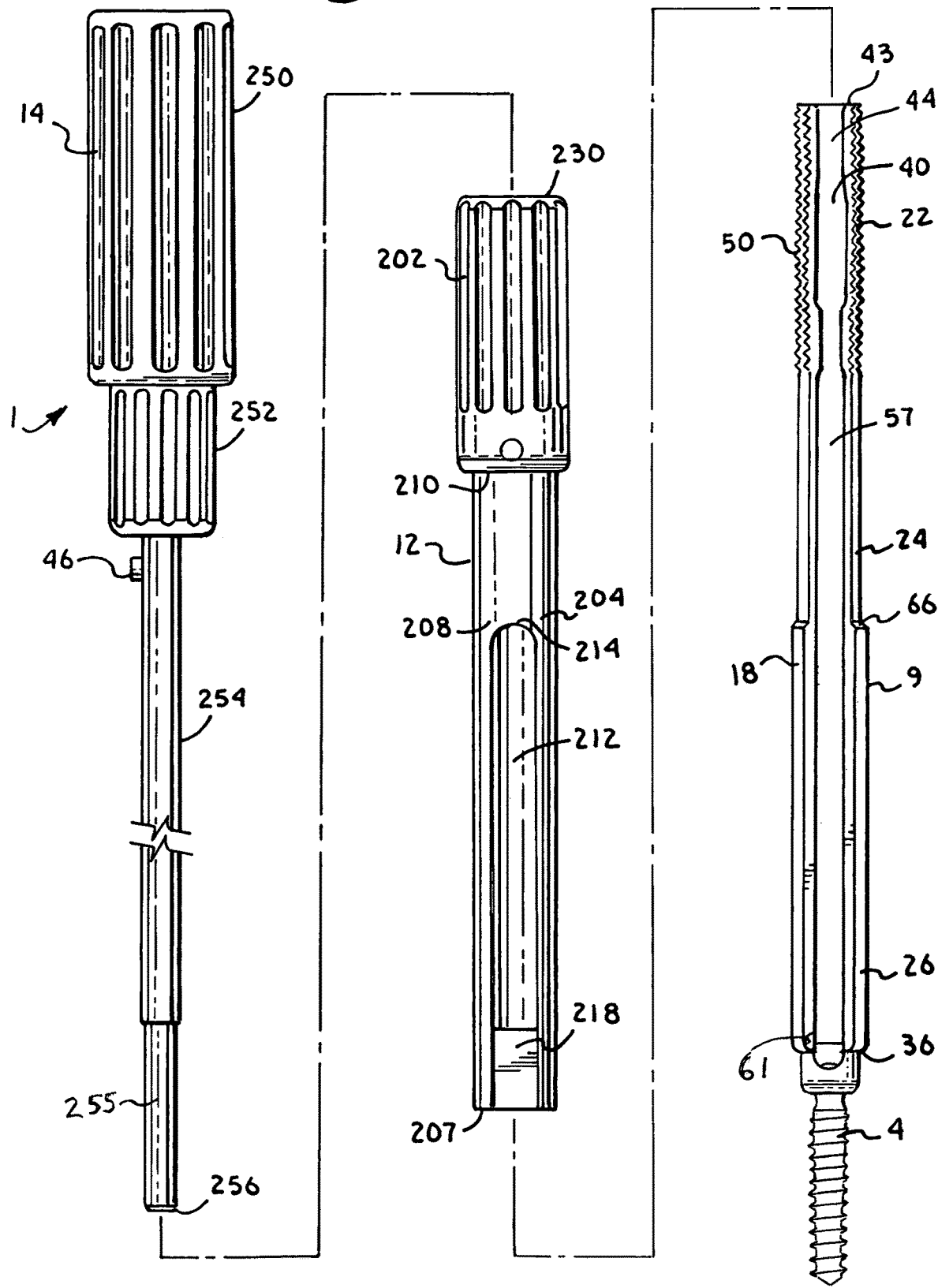
FIG. 1 is an exploded front elevational view of a tool assembly according to the present invention showing a driver tool, a multi-purpose installation tool implant engaging member stabilizer sleeve/tang container and deployer/rod pusher and reducer and an end guide tool shown with an attached polyaxial bone screw.
Figure 12:
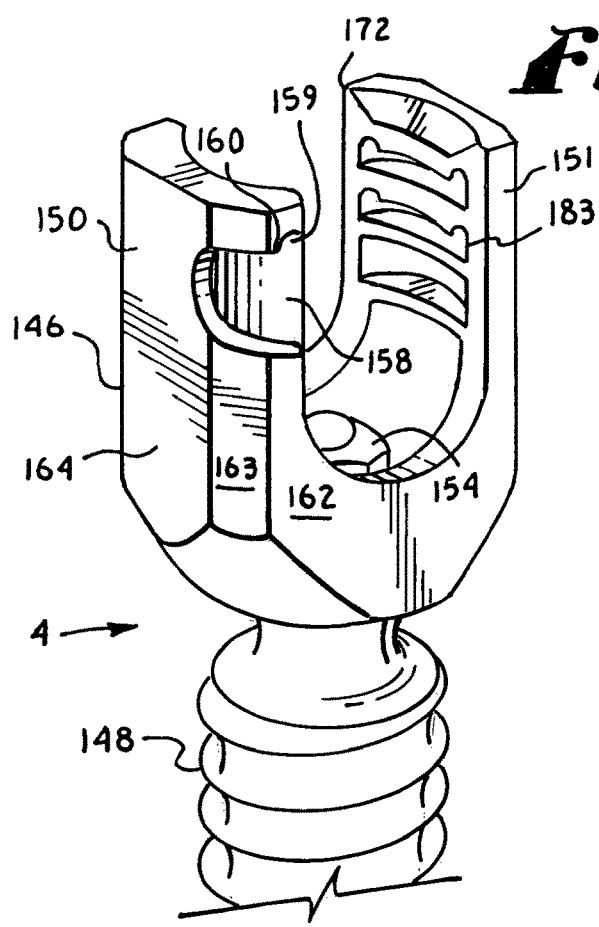
FIG. 12 is an enlarged and fragmentary perspective view of a polyaxial bone screw of the invention.
Figure 13:
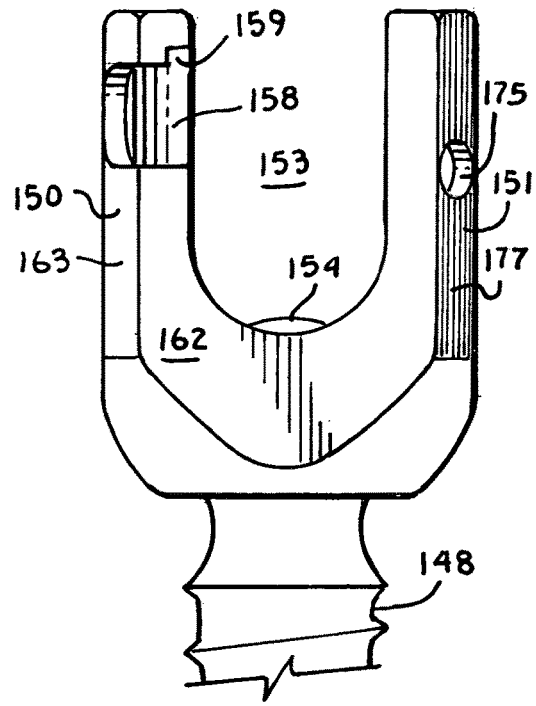
FIG. 13 is an enlarged and fragmentary front elevational view of the polyaxial bone screw of FIG. 12.
Figure 14:
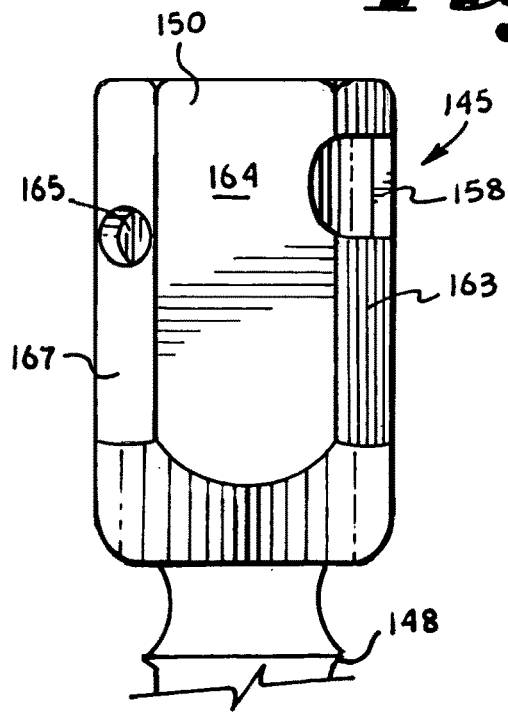
FIG. 14 is an enlarged and fragmentary side elevational view of the polyaxial bone screw of FIG. 12.
Figure 15:
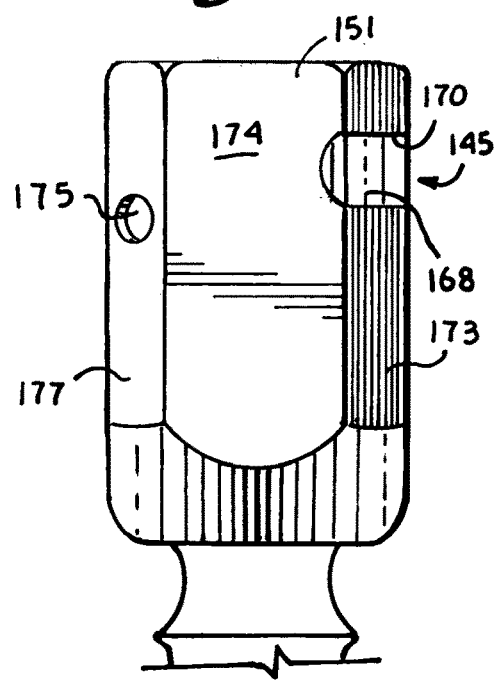
FIG. 15 is an enlarged and fragmentary side elevational view of the polyaxial bone screw of FIG. 12 disposed opposite the side shown in FIG. 14.
Figure 37:
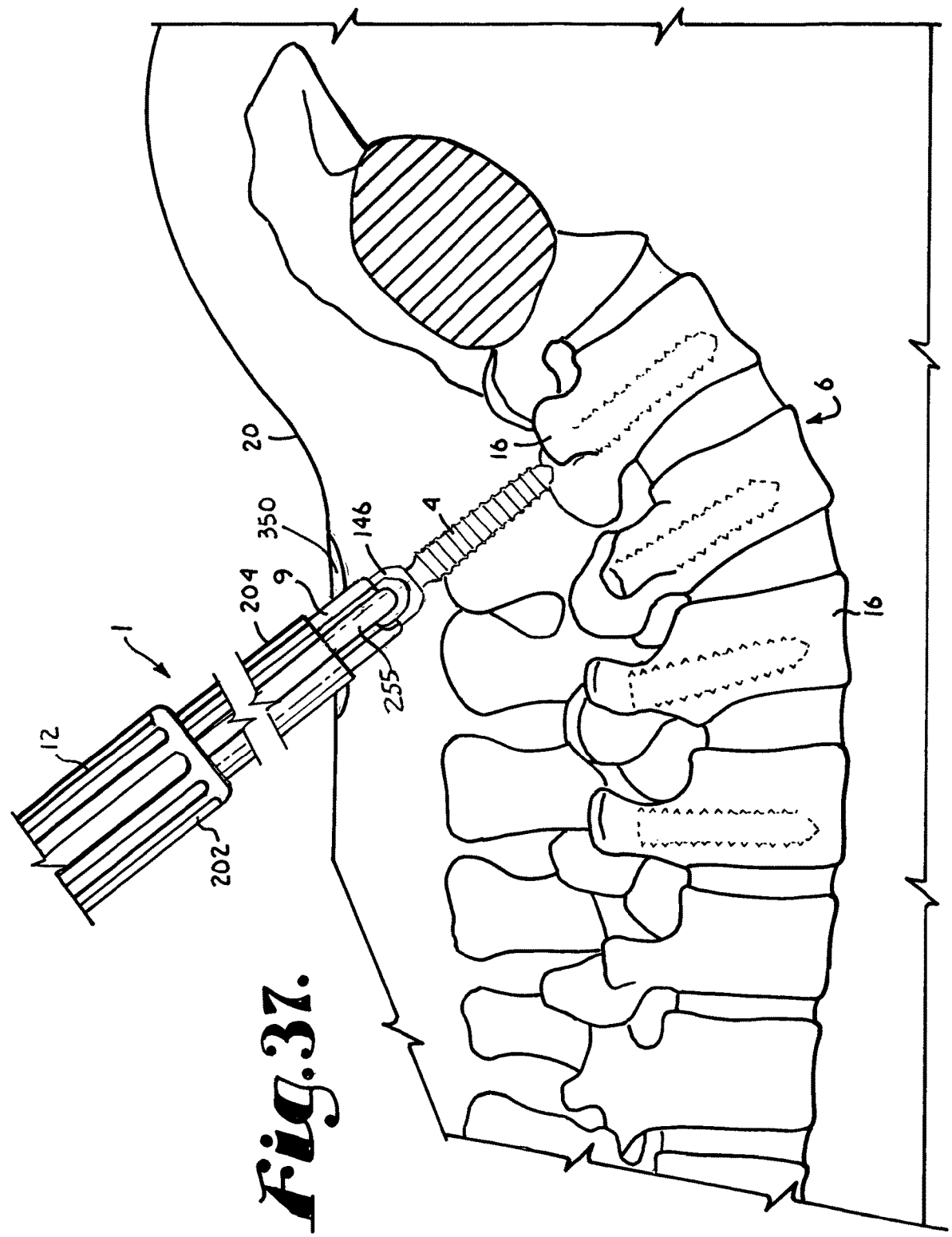
FIG. 37 is a partial and generally schematic view of a patient's spine showing a tool assembly according to the invention with attached bone screw being guided toward the threaded bore in a vertebra in an early stage of a process according to the invention.
Figure 40:
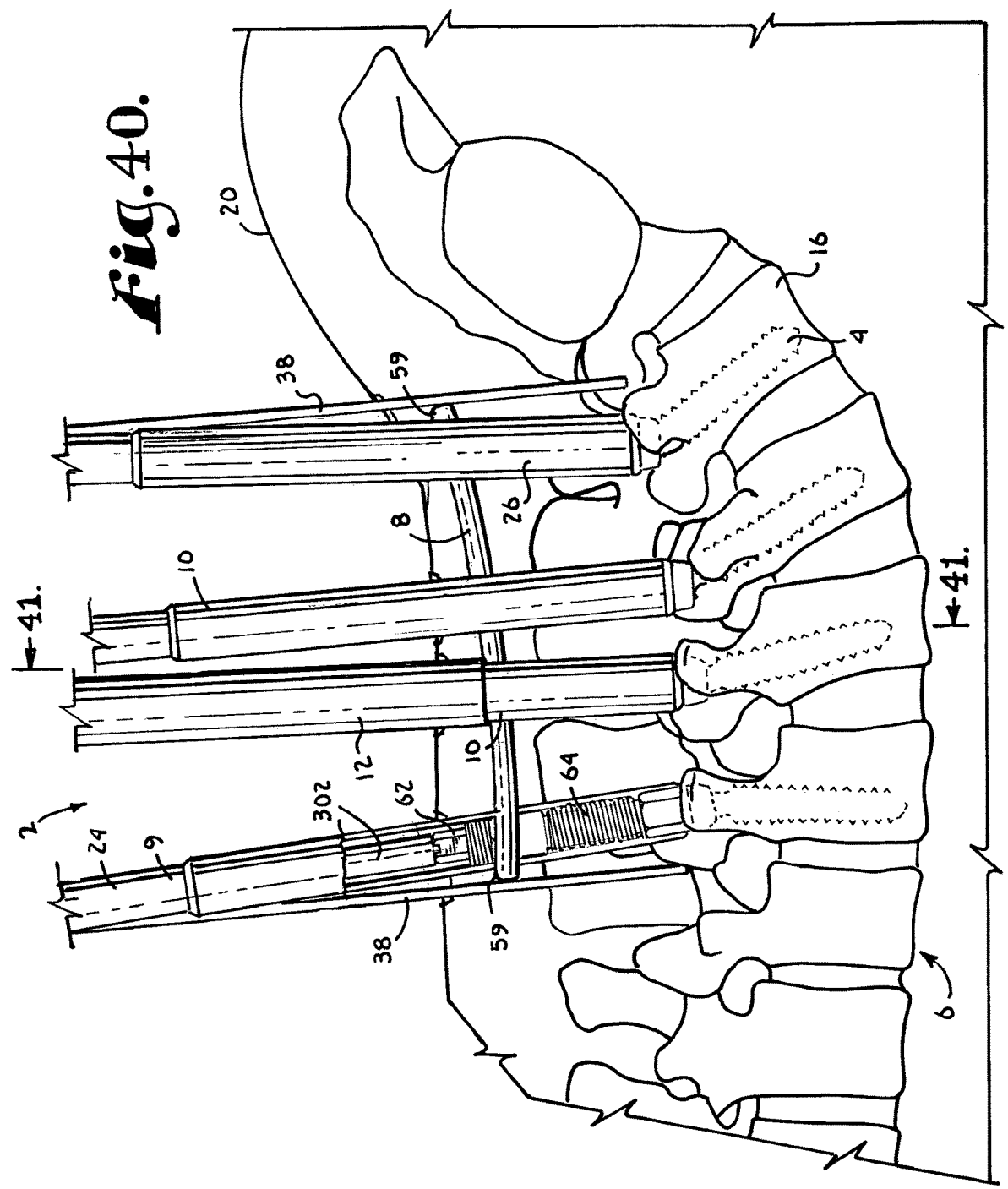
FIG. 40 is a partial and generally schematic view of a patient's spine, showing a pair of end tools with the flexible tangs containing a rod which has now been inserted and a pair of intermediate tools of the present invention with one of the intermediate tools shown with an attached multi-purpose tool in a rod reduction application and one of the end guide tools shown partially cut-away, illustrating a closure top installation tool disposed within the end tool and cooperating with a bone screw closure member, the tools being utilized in an early stage of rod implantation to guide the rod toward the bone screws.

With reference to FIG. 1, and for example, also FIGS. 37 and 40, reference numeral 1 generally designates a tool assembly according to the present invention and reference numeral 2 generally designates a tool set according to the invention, made up of a number and variety of tool assemblies 1 for use in installing a set of bone screws 4 into a patient's spine 6, followed by the installation of an orthopedic spinal rod or longitudinal member 8 into the bone screws 4 in a process according to the present invention.

The tool assembly 1 includes an end guide tool 9 or an intermediate guide tool 10 mated with a multi-purpose installation tool 12 configured to function as a guide tool stabilizer and supporter, a tang container and deployer and a rod pusher and reducer. The tool assembly 1 may further include a driver 14. A set 2 of the illustrated embodiment includes a pair of end guide tools 9 and a plurality of intermediate guide tools 10, which in the illustrated embodiment includes a pair of intermediate guide tools 10 on each side of a patient's spine 6, but which can include none, one or many intermediate guide tools 10 depending upon the particular application, so that one intermediate guide tool 10 is used for each intermediate bone screw 4 to which the rod 8 is to be attached.

The driver 14 is used in conjunction with the guide tool 9 and the guide tool 10 to implant bone screws 4 in the patient's spine 6 and, in particular, in vertebrae 16 along the spine 6 as shown in FIG. 37. Each end guide tool 9 and intermediate guide tool 10 is configured to cooperate with the multi-purpose installation tool 12 to install the rod 8. However, it may be sufficient according to a process of the invention to utilize only one multi-purpose installation tool 12 in a particular tool set 2, as shown in FIG. 40. Rods 8 or other longitudinal members are often installed on both sides of the spine 6 during the same procedure.

It is noted that any reference to the words top, bottom, up and down, and the like, in this application refers to the alignment shown in the various drawing figures, as well as the normal connotations applied to such devices, and is not intended to restrict positioning of the assembly 1 or the tool set 2 in actual use.

The end guide tool 9 is illustrated in FIG. 1 and FIGS. 5 through 8. In particular, each end guide tool 9 has an elongate body 18 that is sized and shaped to be sufficiently long to extend from implanted bone screws 4 through an exterior of a patient's skin 20 so as to provide an outwardly extending and upper handle portion 22 that allows and provides for gripping by a surgeon during procedures utilizing the tool set 2, with or without an attached multi-purpose installation tool 12 and/or driver 14.

Each of the end guide tools 9 further includes an intermediate portion 24 and a lower implant engaging portion 26 which includes opposed implant engaging members for securing one the implants there between. Each end guide tool 9 has a substantially flat back wall 28 joining a pair of substantially cylindrically shaped side walls 32 and 33. The back wall 28 provides a flexible holding structure that includes a pair of parallel slits 34 extending from near the lower handle portion 22 to an end 36 of the tool 9. When pressed upon by a rod 8, a flap or flexible tang 38 disposed between the slits 34 in the back wall portion is configured to flex or spring radially outwardly from the bottom and about the top thereof in a deployed position, as is shown in FIG. 6. The back wall portion flap or tang 38 provides a surgeon with some additional working space and flexibility when working with the rod 8 during surgery, so the rod 8 can extend beyond the bone screws 4 while remaining under resilient tension produced by outward biasing of the flexible back wall portion so that the rod 8 remains in a desired position and under control. Further, the tang or flap 38 also functions to urge the rod 8 toward the other tools in the tool set 2, as shown in FIG. 40 and as will be discussed more fully below.

The upper portion 22 of each end guide tool 9 includes a laterally or sideways opening channel 39, forming a U-shaped cross-section, a C-shaped cross-section, a crescent shaped cross-section or the like having a generally elongate and axially extending opening 40 with a side-to-side width 42. Preferably, the channel 39 mates with other channel structure described below so as to extend the entire length of the end guide tool 9. The opening 40 communicates with and forms part of the channel 39 that opens at an upper end 43 of the guide tool 9 and also opens perpendicularly with respect to a central axis of the guide tool 9 or laterally to one side of the end guide tool 9, thus defining the opening 40. The opening 40 narrows near the upper end 43 providing a slot 44 having a side-to-side width 45 that is smaller than the side-to-side width 42. The slot 44 is configured for sliding engagement with a rotational locking pin 46 disposed on the driver 14 and discussed more fully below. Disposed on either side of the slot 44 are co-planar surfaces 47 and 48 that are parallel with the back wall 28. The surfaces 47 and 48, as well as the back wall 28, provide alignment surfaces when the multi-purpose tool 12 is inserted onto the guide tool 9 discussed more fully below.

The opening 40 is of substantially constant width through a mid-section 48 of the handle portion 22, sufficiently wide to receive additional tools and/or a closure top for sideways loading into the channel 39, as will be discussed below.

The upper portion 22 also includes an outer helically wound discontinuous guide and advancement structure 50 disposed on outer surfaces of both of the substantially cylindrically shaped side walls 32 and 33, which may include conventional helically wound V type threads, buttress threads, helically wound square threads, or other guide and advancement structure to cooperate with equivalent or mateable structure within the multi-purpose installation tool 12 and the driver 14, as described more fully below. The advancement structure 50 extends from near the intermediate portion 24 to the open end 43. The back wall 28 extending between the threaded sides 32 and 33 has an outer substantially planar and smooth surface finish.

Extending from the upper portion 22 and into the intermediate portion 24 of each end guide tool 9 is an outward facing channel 51 that has an opening 52 with a side-to-side width 53 that is somewhat smaller than the width 42 of the upper handle portion 22, such that the channel 51 and opening 52 are sized and shaped to receive and allow passage of certain tools and implants, as described below.

Furthermore, a remaining portion of the end guide tool intermediate portion 24 and the lower portion 26 includes a groove or channel 55, with an elongate, axially extending and radially outward opening 57, having a side-to-side width 58 that is slightly smaller than the width 42 of the opening 40, but larger than the slot width 45 and the opening width 53. The channel opening 57 is disposed opposite the flexible tang or flap 38. All of the channels 39, 51 and 55 communicate with one another and are aligned with one another so as to provide a continuous elongate interior and sideways open passageway with an open side from near the top end 43 to near the bottom 36 thereof. This passageway provides a continuous open path of non-uniform cross-sectional radius throughout from the top 43 to the bottom 36 thereof that is parallel to an elongate axis A of each end guide tool 9. As will be discussed more fully below, each end guide tool channel opening 57 is sized and shaped to slidingly receive a respective end 59 of the rod 8 therein. It is foreseen that one or all of the channel openings forming the open side that extends from near the top end 43 to near the bottom 36 of the guide tool 9 may be sized and shaped to receive the end 59 of the rod 8. It is also foreseen that the rod 8 may be of uniform or non-uniform diameter, regular or uneven surface construction, or smooth or roughened surface finish, and that the channel openings may in turn be sized and shaped to receive such a rod end that may exhibit a greater or smaller width or diameter than at other locations along the rod.

The slits 34 are spaced in order to have a back wall or flap flex region having a size and shape to allow at least partial passage of a respective end 59 of the rod 8 between the side walls 32 and 33. Also located near the end guide bottom 36 is a rod abutment recess 61 that is sized and shaped for the purpose of bridging the rod 8 when the end guide tool 9 is rotated for removal, as described below. However, it is foreseen that other removal means could be used. The end guide tool 9 also receives a closure top 62, as will be described below. Still further, near the bottom 36 of each of the end guides 9 on inner surfaces of the side walls 32 and 33, is a helical wound, discontinuous guide and advancement structure 64 which may include conventional helically wound V-shaped threads, buttress threads, reverse angle threads, helically wound square threads, or other guide and advancement structure to cooperate with equivalent or mateable structure within the bone screw heads 4 and on the closure top 62, as also described below.

At the lower portion 26, the substantially cylindrical side walls 32 and 33 include an outer radially extending bevel 66 and substantially cylindrical outer side walls 68 and 69, respectively. The walls 68 and 69 uniformly increase the thickness of the respective side walls 32 and 33, resulting in a substantially cylindrical cross-section of greater diameter than a diameter created by an outer surface of the side walls 32 and 33 at the intermediate portion 24.

As will be discussed more fully below, in addition to increasing the diameter, the walls 68 and 69 are configured with co-planar front walls or facets 70 and co-planar back walls or facets 71 with the facets 70 being disposed parallel to the facets 71, providing for alignment and mating with an interior of the multi-purpose installation tool 12 to ensure that the end guide tool 9 is retained in a selected, non-rotatable position with respect to the multi-purpose installation tool 12 when installed therein. Each of the walls 68 and 69 can include an abutment pin 67 located at an outer surface thereof and near the bottom or end 36. The pin 67 may serve as a stop for the multi-purpose installation tool 12 as will be described more fully below; however, such a pin stop is not always needed.

Near the end or bottom 36 of each end guide tool 9, disposed on an inner surface of each of the side walls 32 and 33, is a radially inward facing attachment structure, generally 72, that will be described below in conjunction with a similar structure on the intermediate guide tool 10 and the bone screw 4.

Each of the intermediate guide tools 10, specifically illustrated in FIGS. 2 to 4, have a somewhat similar overall shape when compared to the end guide tools 9 in that both are preferably of the same axial length and width and also have much structure in common; however with certain differences as noted. Each intermediate guide tool 10 has an overall elongate body 74 with an upper handle portion 76, an intermediate portion 77 and a lower implant engaging portion 78 which includes opposed implant engaging members for securing one of the implants there between. In the upper portion 76, the body 74 is generally C-shaped defining a radially outward opening 79 communicating with an elongate and axially extending channel 80 defined by a rear wall 81 having a lower web edge 96 and side walls 82 and 83. With reference to FIG. 2, the channel 80 front opening 79 extends parallel to an axis B of the body 74 and has a side-to-side width 85 configured to receive tools and elements described below.

Similar to the end guide tool 9, the opening 85 narrows near an upper end 87 providing an elongate slot 88 having a side-to-side width 89 that is smaller than the width 85. The slot 88 is configured for sliding engagement with the pin 46 disposed on the driver 14 and discussed more fully below. Disposed on either side of the slot 88 are co-planar surfaces 91 and 92 that are parallel with the rear wall 81. The surfaces 91 and 92, as well as the rear wall 81, provide alignment surfaces when the multi-purpose tool 12 is inserted onto the guide tool 10, discussed more fully below. Below the slot 88, the side-to-side opening width 85 is substantially constant through a mid-section 90 of the handle portion 76, sufficient to receive additional tools and/or a closure top, as will be discussed below.

The upper or handle portion 76 also includes an outer helically wound discontinuous guide and advancement structure 93 disposed on outer sides of both of the substantially cylindrically shaped side walls 82 and 83, which may include conventional helically wound V-threads, helically wound square threads, buttress threads or other guide and advancement structure to cooperate with equivalent or mateable structure within the multi-purpose installation tool 12 and the driver 14 as described more fully below. The advancement structure 93 extends from near the intermediate portion 77 to the open end 87. An outer surface of the rear wall 81 extending between the threaded sides 32 and 33 is substantially planar and smooth.

The upper or handle portion 76 further includes an outward facing channel 94 communicating with the channel 80. The channel 94 is defined in part by a rear wall or web 95 having a lower end with the web edge 96, the wall 95 being integral with the wall 81. Communicating with the channel 94 is an elongate and axially extending opening 98 having a side-to-side width 99 that is somewhat smaller than the width 85 of the opening 79. The opening 98 is further defined by the walls 82 and 83. The channel 94 and opening 98 are configured to receive, contain and allow translational movement therealong or rotational relative movement of certain tools, as described more fully below. Although not shown in the drawings, it is foreseen that the channel 94, channel opening 98 and rear wall or web 95 may extend into the intermediate portion 77 to provide greater strength and stability to the lower portion 78 of the intermediate tool 10, with the opening 98 also extending into the lower portion 78 providing greater retention of small tools or parts being inserted through the channel 94.

The intermediate portion 77 of the intermediate tool 10 includes two spaced side walls or legs 102 and 103, extending from and integral with the side walls 82 and 83, respectively. The legs 102 and 103 have outer surfaces that are partially cylindrical.

Similar to the end tool 9, at the juncture of the intermediate portion 77 and the lower portion 78, each of the legs 102 and 103 include an outwardly facing radially extending bevel 106 integral with substantially cylindrical outer side walls 107 and 108, respectively. The outer walls 107 and 108 extend along the length of the lower portion 78 and uniformly increase the thickness of the respective legs 102 and 103, resulting in a substantially cylindrical cross-section of greater outer diameter at the lower portion 78 than an outer diameter created by the outer surfaces of the legs 102 and 103 along the intermediate portion 77. As will be discussed more fully below, in addition to increasing the diameter, the walls 107 and 108 are configured with co-planar front facets or walls with flat surfaces 109 and co-planar rear facets or walls with flat surfaces 110, the facets 109 disposed parallel to the facets 110, providing for alignment with an interior of the multi-purpose installation tool 12 to ensure that the intermediate guide tool 10 is properly mated with and retained in a selected, non-rotatable position with respect to the multi-purpose installation tool 12 when installed therein.

Along both the intermediate and lower portions 77 and 78 of the intermediate tool 10, the legs 102 and 103 define an elongate and axially extending passthrough slot 111 sized and shaped to slidingly receive the rod 8. The slot or opening extends from the lower edge of the web end 96 of the rear wall 95 to an open end or bottom 112 of the tool 10 configured to secure an open ended spinal surgery implant there between.

Near the bottom 112 of each implant engaging leg member 102 and 103 of the intermediate guide tool 10 is a helically wound but discontinuous square thread 114 and it is foreseen that other type of guide and advancement structure may be utilized such as helically wound flange forms, reverse angle threads, buttress threads, etc. The thread form 114 cooperates with the closure top 62, as described below. The lower end of each leg 102 and 103 of the intermediate guide tool 10 also includes a cutout or rod-abutment recess 116 similar to the recess 61 described with respect to the end tool 9. Each of the walls 107 and 108 can include an abutment pin 118 located at an outer surface thereof and near the bottom or end 112. The pin 118 may serve as a stop for the multi-purpose installation tool 12 as will be described more fully below.

Also near the end or bottom 112 of each leg 102 and 103 of the intermediate guide tool 10, disposed on inner substantially cylindrical surfaces 120 and 121, respectively, is a radially inward facing attachment structure, generally 124, substantially similar to the structure 72 disposed on the end guide tool 9. The structure 124 will be described herein in conjunction with the bone screw 4.

With reference to FIGS. 9-11, the embodiment shown includes an attachment structure 124 having a first projection, stop or pin 126 in spaced relation with a second smaller projection, stop or pin 127, both pins being disposed on the surface 120. In the embodiment shown, the structure 123 further includes a cooperating third projection, stop or pin 130 in spaced relation with a fourth smaller projection, stop or pin 131, the pins 130 and 131 being disposed on the surface 121.

The larger pins 126 and 130 are substantially configured the same, both being substantially rounded, radially inward projecting nodules, each having a ridge or lip 132 and 133, respectively, projecting upwardly toward the guide and advancement structure 114 and that preferably follows the curvature of the respective leg inner surface 120 and 121.

The lips 132 and 133 with respective surfaces 120 and 121 define slots 134 and 135, respectively, for receiving the bone screw 4 as will be discussed more fully below. The pin 126 is configured slightly larger than the pin 130, requiring similar modification in the bone screw 4, resulting in a method of operation wherein the bone screw 4 may only be mated with the guide 9 or 10 from a single direction, ensuring appropriate alignment between the bone screw 4 and guide tool advancement structure 114 with respect to the installment of the closure top 62.

Each of the larger pins 126 and 130 is also disposed at substantially the same distance from respective bottom surfaces 138 and 139, at the end 112 of the guide tool 10 and adjacent a rod-abutment recess 116. Furthermore, each of the larger pins 126 and 130 is also disposed at substantially the same distance from respective parallel seating surfaces 140 and 141, that form a base of the guide and advancement structure 114. Additionally, in this embodiment the pins 126 and 130 are disposed in diametrically opposed relation when viewed in cross-section as shown in FIG. 10.

The smaller pins 127 and 131 are also substantially configured the same, the pin 131 being slightly larger than the pin 127, but otherwise both pins 127 and 131 being substantially rounded, radially inwardly projecting nubs, each disposed at substantially the same distance from the respective bottom surfaces 138 and 139 and the respective seating surfaces 140 and 141. Furthermore, the pins 127 and 131 are disposed in diametrically opposed relation when viewed in cross-section as shown in FIG. 10. Each of the pins 127 and 131 are disposed closer to the respective end surfaces 138 and 139 than are the larger pins 126 and 130. It is noted that other orientations and pin sizes may be utilized according to the invention, with the pin sizes and locations cooperating with respective features on the bone screws 4. Preferably, the pins are of different sizes to provide for mating of the guide tool 9 or 10 with the bone screw 4 from a single direction, resulting in a desired alignment between the bone screw 4 guide and advancement structure 114 and the closure top 62 guide and advancement structure.

The pins 126, 127, 130 and 131 cooperate and mate with the bone screw 4, at a receiver portion, generally identified by the reference numeral 145, of a head 146 thereof. With reference to FIGS. 12-15, each of the bone screws 4 further includes a threaded shank 148 attached to the head 146, the shank 148 for screwing into and seating in a vertebra 16 that is part of the human spine 6. The head 146 includes first and second arms 150 and 151 that define a rod receiving channel 153 passing therethrough. Each of the bone screw shanks 148 includes an upper portion 154 that extends into the head 146 and is operationally secured therein, so that the head 146 is rotatable on the shank 148 until locked in position through engagement with the rod 8 under pressure.

The receiver portion 145 is disposed on outer surfaces of the arms 150 and 151. The receiver portion 145 of arm 150 includes a slot or groove 158 communicating with a recess 159 defined in part by a flange 160. The groove 158 and recess 159 open at a front surface 162 of the arm 150 and extend across a facet 163 and into a side surface 164 thereof. With reference to FIG. 21, the groove 158 is configured to mate with the large pin 126 with the lip 132 extending into the recess 159 and the flange 160 disposed in the slot 134 when the guide tool 10 is attached to the bone screw head 146. The width of the slot 134 is sized to prevent passage therethrough of the pin 126 except by twisting or rotational relative movement therebetween. The receiver portion 145 of the arm 150 further includes a rounded aperture 165 disposed substantially centrally on a face or facet 167 of the arm 150, the facet 167 disposed adjacent to the side surface 163. The aperture 165 is configured to mate with the small pin 127.

Similar to the arm 150, the receiver portion 145 of the arm 151 defines a groove 168 communicating with a recess 169 defined in part by a flange 170. The groove 168 and recess 169 open at a back surface 172 of the arm 151 and extend across a facet 173 into a side surface 174 thereof.

Similar to what is shown in FIG. 21 with respect to the arm 150, the groove 168 is configured to mate with the large pin 130 with the lip 133 extending into the recess 169 and the flange 170 disposed in the slot 135 when the guide tool 10 is attached to the bone screw head 146. The receiver portion 145 of the arm 151 further includes a rounded aperture 175 disposed substantially centrally on a face or facet 177 of the arm 151, the facet 177 disposed adjacent to the side surface 173. The aperture 175 is configured to mate with the small pin 131.

In the embodiment shown, to attach the bone screw head 146 to the guide tool 10, the guide tool 10 is rotated about its axis B such that the legs 102 and 103 are lowered into place as shown in FIGS. 17 and 18, with the facets 167 and 177 of the head 146 disposed between the guide tool legs 102 and 103, with the facet 167 adjacent the leg 102 and the facet 177 adjacent the leg 103, thereby aligning the groove 158 with the large pin 126 and the groove 168 with the large pin 130. The head 146 may then be twisted into place as shown by the arrow T in FIGS. 18, 19 and 20. The legs 102 and 103 may splay slightly as the head is twisted into place, but come to rest in a generally non-splayed configuration and held in place by the structure of the attachment mechanism to resist splaying.

In order to disengage the guide tool 9 or the guide tool 10 from the bone screw 4, the guide tool 9, 10 is rotated counterclockwise from an attaching configuration (opposite to the arrow T), when viewing from the top so as to disengage the lips 132 and 133 from the recesses 159 and 169, respectively. In this manner, end guide tools 9 and intermediate guide tools 10 that have previously twisted on, now twist off of respective bone screws 4.

While a preferred embodiment of the invention has the respective pins of the attachment structure on the guide tools and the grooves on the bone screw heads, it is foreseen that these elements could be reversed in total or part in accordance with the invention. Also, other suitable attachment structure could be used, such as sloped or tapered undercut surfaces on the screw heads that overlap, mate and interlock with radially or linearly projecting structure on or near the ends of the guide tools. Such projecting structure can be snapped on or clipped on and translated up to provide for anti-splay overlapping surfaces.

In the embodiment shown, the recesses 61 and 116 disposed on the respective guide tools 9 and 10 are sized, shaped and positioned so that when the rod 8 is located in the bone screws 4, the guide tools 9 and 10 can rotate about respective axes A and B, with the recess 61 and 116 allowing the respective guide tool 9 and 10 to straddle over the rod 8, thereby allowing the guide tool 9 and 10 to twist relative to the bone screw 4 and free the attachment structures 72 and 124 from the receiver portion 145 of the bone screw 4 and thereafter be removed after all procedures are complete, as described below.

The closure top 62 closes between the spaced bone screw arms 150 and 151 to secure the rod 8 in the channel 153. The closure top 62 can be any of many different plug type closures. With reference to FIGS. 46-48, preferably the closure top 62 has a cylindrical body 180 that has a helically wound mating guide and advancement structure 181. The guide and advancement structure 181 can be of any type, including V-type threads, buttress threads, reverse angle threads, or square threads. Preferably the guide and advancement structure 181 is a helically wound flange form that interlocks with a reciprocal flange form as part of a guide and advancement structure 183 on the interior of the bone screw arms 150 and 151.

A suitable locking guide and advancement structure of this type is disclosed in U.S. Pat. No. 6,726,689 from Ser. No. 10/236,123 which is incorporated herein by reference. Referring to FIGS. 49 to 59, the reference numeral 400 generally designates a gripping interlocking form arrangement incorporating a non-linear or compound surface which embodies the present invention. The interlocking form arrangement 400 includes an external interlocking form 402 and internal interlocking form 404 which have respective thrust surfaces 406 and 408 (FIG. 4) and which are used as pairs. The interlocking form arrangement 400 may be used on any of a number of interlocking formed devices, such as an implanted bone fixation system, including a receiver or open headed implant member which receives a closure or closure member to secure a fixation member therein. In the interlocking form arrangement 400, the thrust surfaces 406 and 408 are non-linear or compound in such a manner as to resist tendencies of arms 432, for example, to splay or expand when the closure member 410 is rotated therein.

Figure 49:
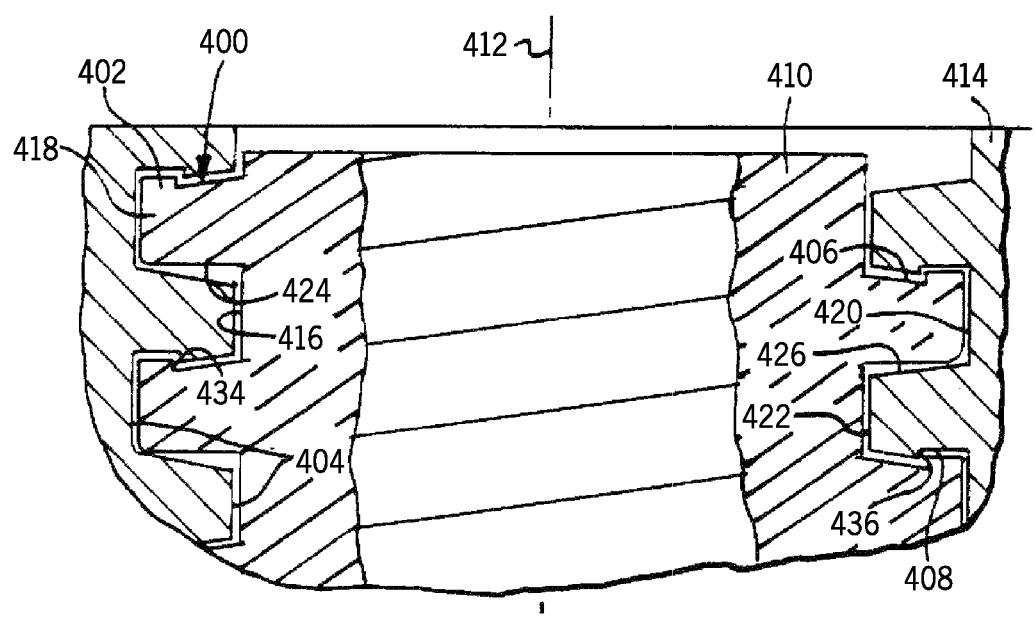
FIG. 49 is an enlarged fragmentary side elevational view of the bone screw head with the closure installed therein, the closure and bone screw head incorporating the interlocking form according to the present invention with portions broken away to show detail thereof.

The interlocking forms 402 and 404 are helical and are intended to advance the closure member 410 linearly along the axis of rotation 412 of the closure member 410 and the interlocking forms 402 and 404 relative to another member as the closure member 410 is rotated relative to a bone screw 4. A spatial reference for such rotation and linear movement is along the axis 412 (FIG. 49). The axis 412 locates the coincident axes of the external or radially outward interlocking form 402 of a base 410 (e.g., a closure member 410) and the internal or radially inward interlocking form 404 of a head 414, when the base 410 is inserted into the head 414 by starting at the top of the interlocking form 404 (top is up in FIG. 49) and rotated. The base 410 has a basic cylindrical shape, and the external interlocking form 402 includes a root 416 and a crest 418 formed by cutting a helical wound channel of the desired cross section into the original surface of the base 410. The crest 418 of the external interlocking form 402 has a greater radius than the root 416. In a like manner, the internal interlocking form 404 of the head 414 of a screw 4 has a helical channel under cut thereinto, forming a root 420 and crest 422. The root 420 of the internal interlocking form 404 has a greater radius than the crest 422.

The thrust surfaces 406 and 408 respectively of the external and internal interlocking forms 402 and 404 engage frictionally when the base 410 is rotated into the head 414. The thrust surfaces 406 and 408 are located on the trailing sides respectively of the crests 418 and 422, as referenced to the tightening direction movement of the base 410 into the head 414. In general, there is minimal contact between the clearance surfaces 424 and 426 when the base 410 is rotated in a tightening direction into the screw head 4 to allow rotation. The clearance surfaces 424 and 426 may frictionally engage when the base 410 is rotated in a reverse direction to remove it from the screw head 414.

Frictional engagement of the thrust surfaces 406 and 408 due to rotation causes the base 410 to be advanced linearly along the axis 412 into the screw head 414. However, once the base 410 "bottoms out" by contact of a lower surface 428 or a set point 430 with a rod 432 and the rod 432 is unbent and pushed downwardly as far as it will go into a channel or seat of the head 414, further rotation of the base 410 cannot result in further linear movement of the base 410 within the head 414. The interlocking forms 402 and 404 thereafter are radially locked together and each turn or pass of the forms 402 and 404 is preferably sufficiently snug with respect to turns of the opposite interlocking form to prevent either form 402 or 404 from slipping or sliding radially past one another upon application of additional torque or with application of forces due to usage by the patient.

The various compound, complex, or non-linear interlocking form arrangements of the present invention are intended to resist splaying tendencies of the arms 432. In particular, each thrust surface 406 and 408 of the interlocking forms 402 and 404 have a gripping, blocking or splay resisting surface 434 or 436 respectively which is oriented in such a direction as to resist splaying of the arms 432 of the screw head 414 when the base 410 is rotated to a high degree of torque. On the external interlocking form 402, the splay resisting surface 434 is directed generally toward or faces the axis 412. Conversely, on the internal interlocking form 404, the splay resisting surface 436 is directed generally away from or faces away from the axis 412. Each of the surfaces 434 and 436 in this manner wrap over or around the opposite and block substantial radially relative movement there between. It is especially noted that the surfaces 434 and 436 are extensions of the interlocking forms 402 and 404 in an axial direction (that is parallel to the axis 412 or up and down as seen in FIG. 49). This axial extension is spaced away from the juncture of the interlocking forms 402 and 404 with the base 410 and screw 4. It is foreseen that such an extension can take many shapes and configurations (some of which are shown herein) and may also functionally be depressions or grooves. In each case the paired interlocking forms, such as forms 402 and 404, overlap each other and are snug about each other so as to prevent substantial relative radial slippage or movement between them during and after assembly of the base 410 into the bone screw 4.

Figure 50:
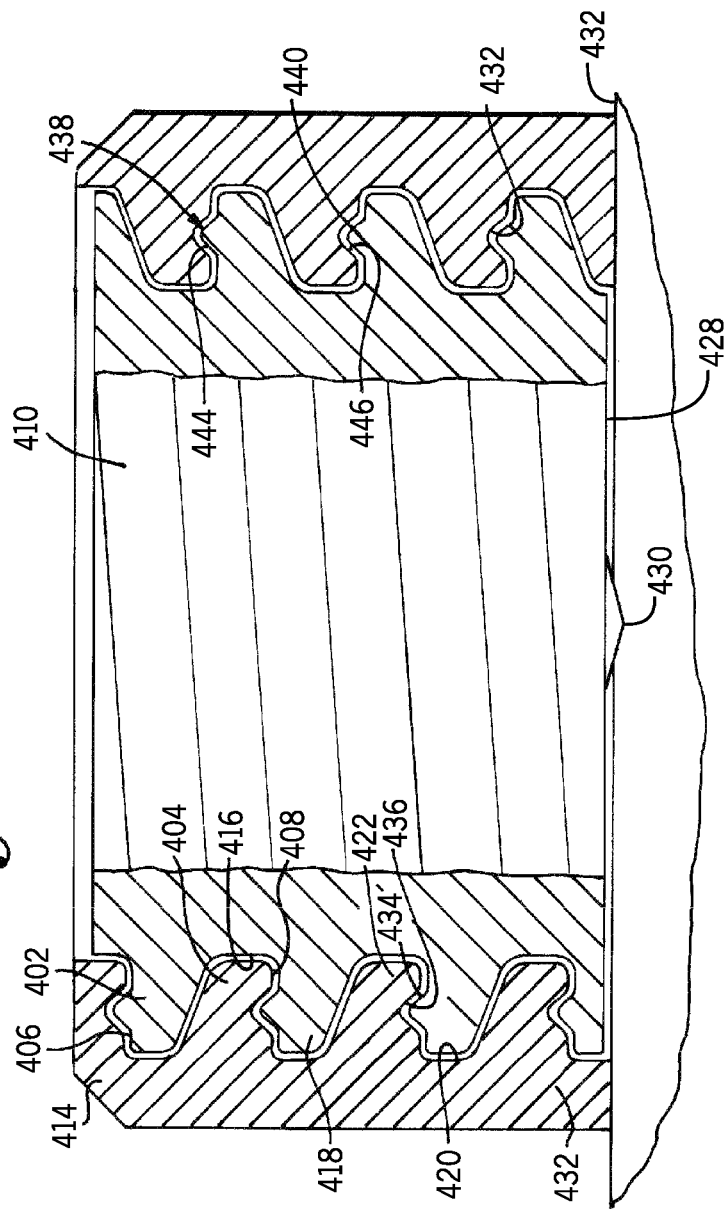
FIG. 50 is a view similar to FIG. 49 and illustrates details of first modified bone screw and closure showing a medial bead embodiment of an interlocking form of the present invention.

FIG. 50 illustrate a non-linear or compound thrust surface interlocking form arrangement 438 which is of a medial bead interlocking form type. The interlocking form arrangement 438 is a thrust surface 406 located on a plug 410 and internal interlocking form 404 with thrust surfaces 408 within a head 414 of a bone screw 4. The thrust surfaces 406 and 408 are contoured to provide complementary, interacting, splay resisting surfaces 434 and 436 on the external and internal interlocking forms 402 and 404 respectively. The external interlocking form 402 is provided with a bead 440 on the thrust surface 406, and the internal interlocking form 404 is provided with a complementary channel or groove 442 formed into the thrust surface 408. The illustrated thrust surfaces 406 and 408 are substantially perpendicular to the axis 412; however, such surfaces may alternatively be angled somewhat with respect to the axis 412 so as to slope downward or upward as the surface extends radially outward.

The bead 440 is located at a radius which is between or medial with respect to the root 416 and crest 418 of the external interlocking form 402. Similarly, the groove 442 is located at a radius which is medial to the root 420 and crest 422 of the internal interlocking form 404. The illustrated bead 440 and groove 442 are rounded and somewhat triangular in cross section. Alternatively, the bead and groove 440 and 442 could be pointed and triangular, squared off, or semicircular. It should also be noted that the bead and groove 440 and 442 could be replaced by a medial groove formed in the external interlocking form 402 on the thrust surface 406 and a medial bead formed on the thrust surface 408 of the internal interlocking form 404. An inwardly facing surface 444 of the bead 440 forms the splay resisting surface 434 thereof, while an outwardly facing surface 446 of the groove 442 forms the splay resisting surface 436 of the groove 442. Engagement of the splay resisting surfaces 444 and 446, respectively of the bead 440 and groove 442, resists tendencies of the arms 432 of the screw head 414 to splay when the closure base 410 is rotated into the head 414.

FIGS. 51 to 59 illustrate further variations in the paired interlocking forms of the present invention. In each case the base closure and bone screw, except as noted with respect to the interlocking forms, of the variations shown in FIGS. 51 to 59 are essentially the same as those shown in FIG. 49, so only differing detail of the interlocking form structure will be described in detail and reference is made to the description given for FIG. 49 for the remaining detail.

Figure 51:
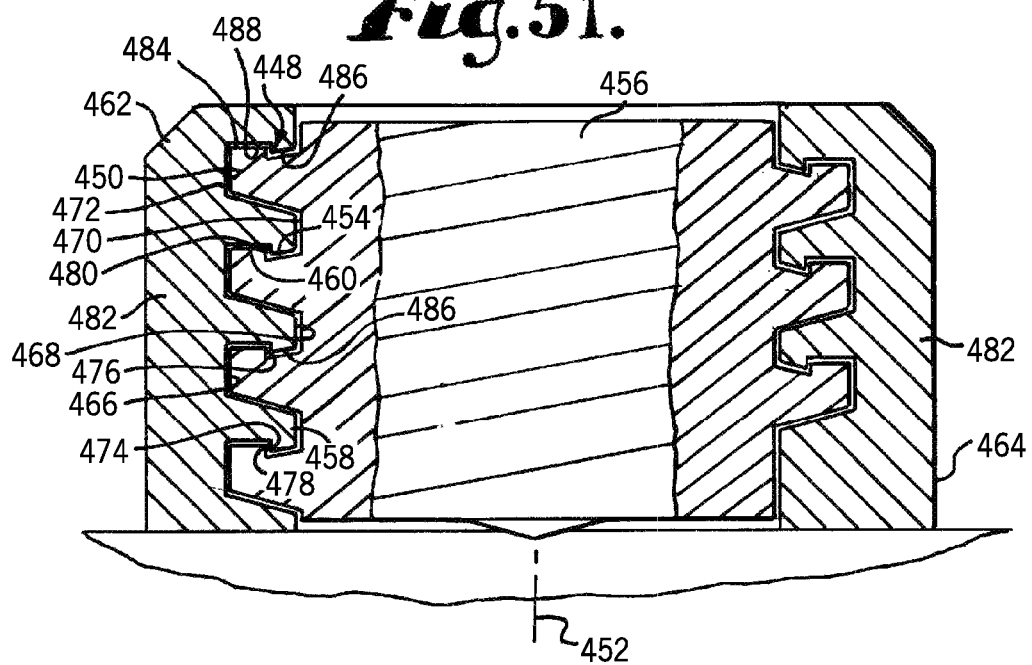
FIG. 51 is view similar to FIG. 49 and illustrates details of a second modified bone screw and closure showing an axial aligned shoulder embodiment of an interlocking form of the present invention.

In FIG. 51, a guide and advancement structure 448 includes the external interlocking form 450 having an axially aligned shoulder or flange-like shaped configuration when view in cross section in a plane passing through an axis of rotation 452. The interlocking form 450 has a thrust surface 454 on a base 456. The structure 448 also has an internal interlocking form 458 with a thrust surface 460 within the head 462 of a bone screw 464. The internal interlocking form 458 has a root 466 and a crest 468, while the external interlocking form 450 includes a root 470 and crest 472. The thrust surface 454 of the external interlocking form 450 includes an axially oriented or cylindrical shoulder 474 which forms a splay resisting surface 476 thereof.

Figure 52:
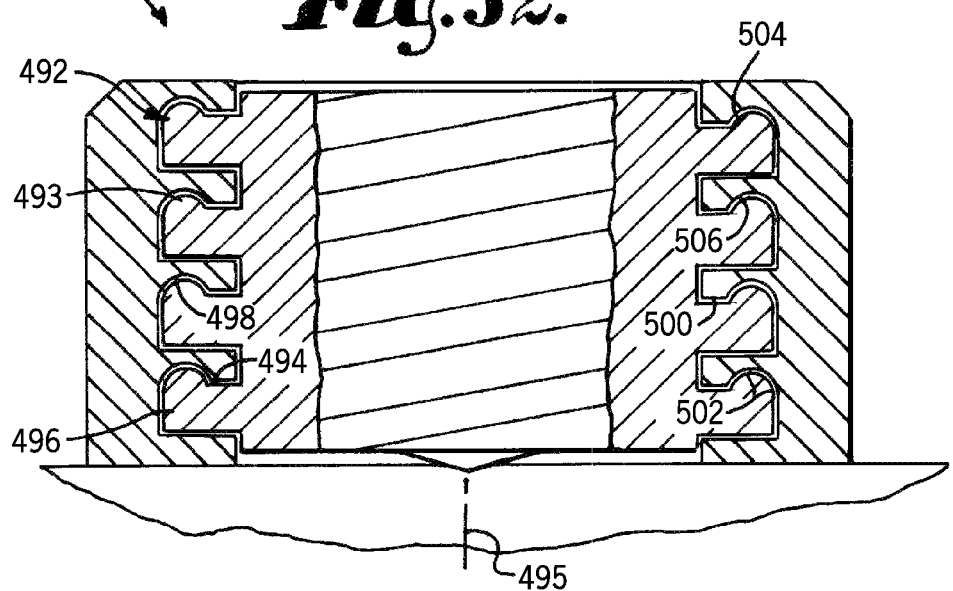
FIG. 52 is a view similar to FIG. 49 and illustrates details of a third modified bone screw and closure showing an axial bead embodiment of an interlocking form of the present invention.
Figure 53:
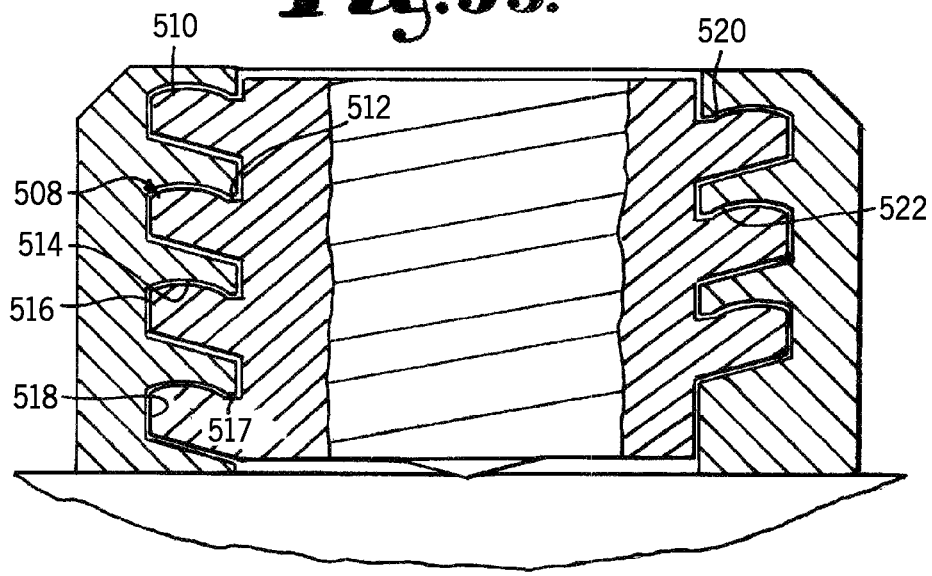
FIG. 53 is a view similar to FIG. 49 and illustrates details of a fourth modified bone screw and closure showing a shallow axial bead embodiment of an interlocking form of the present invention.

Similarly, the thrust surface 460 of the internal interlocking form 458 includes a mating or complementary axially oriented or cylindrical shoulder 478 which forms a splay resisting surface 480. Engagement of the splay resisting surfaces 476 and 480 resists tendencies of the arms 482 of the head 462 to splay when the plug or base 456 is rotated into the head 462 and torqued tightly or at later times during usage. It is foreseen that a variation of the axial shoulder interlocking form would provide shoulders at inclined angles (not shown) to the axis 412. The illustrated splay resisting shoulder 474 is formed by a rectangular cross section bead 484 formed on the thrust surface 454 of the external interlocking form 450. Similarly, splay resisting shoulder 478 is formed by a somewhat rectangularly cross section shaped bead or foot portion 486 adjacent a groove 488 for receiving bead 484 and formed in the thrust surface 460 of the internal interlocking form 458. The interlocking forms 450 and 458 have a general flange-like shape configuration when viewed in cross section that is also some what L-shaped with the beads 484 and 486 forming feet of the flange shape that overlap and lock so as to prevent substantial radial movement of the arms 482 of the bone screw 464 relative to the closure plug base 456. FIGS. 52 and 53 illustrate further variations of the axial shoulder interlocking structure 490 and 508 respectively in the form of a rounded axial bead interlocking form 492 shown in FIG. 52 and a shallow rounded axial bead interlocking form 510 in FIG. 53. The rounded axial bead interlocking form 492 includes a rounded bead 493 projecting in a direction parallel to an axis 495. The bead 493 is formed on a thrust surface 494 of an external interlocking form 496 and a rounded groove 498 is formed on a thrust surface 500 of an internal interlocking form 502. The bead 493 includes a splay resisting surface 504, while the groove 498 also includes a splay resisting surface 506.

In a similar manner, the shallow rounded axial bead interlocking form 508 includes a shallow rounded bead 510 formed on a thrust surface 512 of an external interlocking form 516 and a shallow rounded groove 514 formed on a thrust surface 517 of an internal interlocking form 518. The bead 510 includes a splay resisting surface 520, and the groove 514 includes a splay resisting surface 522. The surfaces 520 and 522 engage and abut to resist splaying or significant radial separation movement therebetween.

Figure 54:
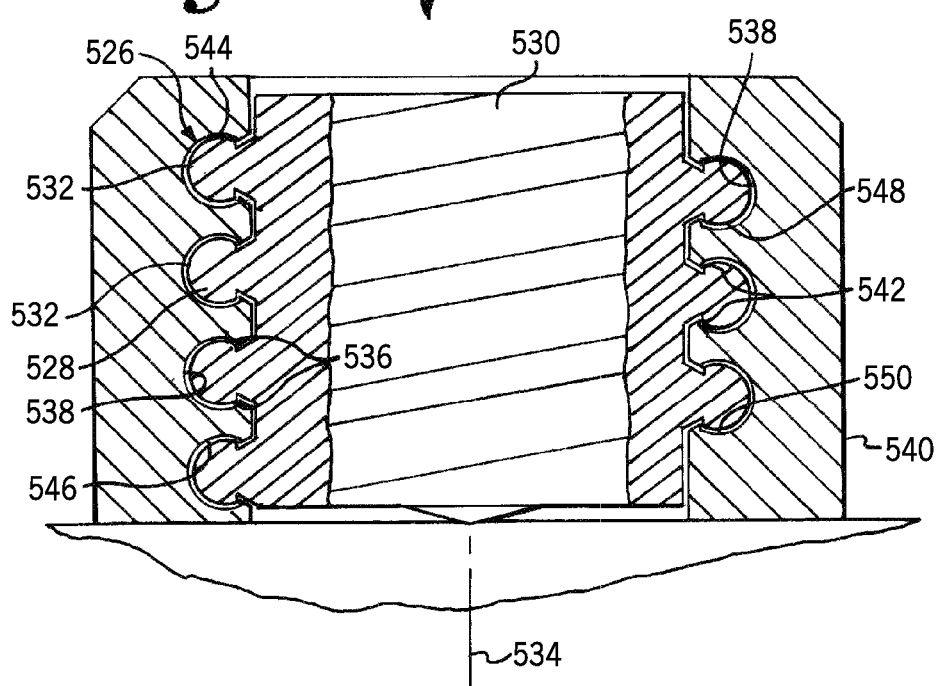
FIG. 54 is a view similar to FIG. 49 and illustrates details of a fifth modified bone screw and closure showing a radial bead embodiment of an interlocking form of the present invention.

FIG. 54 illustrates a radial bead embodiment of an implant 524 having a guide and advancement structure 526. The structure 526 includes a rounded external and bead interlocking form 528 projecting radially from a base 530 and forming a crest 532. The bead interlocking form 528 has a pair of splay resisting surfaces 536 facing generally toward an axis 534 of rotation of the base 530. A complementary groove internal interlocking form 538 is part of a screw head 540. The head interlocking form 538 has a pair of splay resisting surfaces 542 facing generally away from the axis 534. The structure 526 has the splay resisting surfaces 536 and 542 on thrust surfaces 544 and 546 respectively of the interlocking forms 528 and 538, as well as on clearance surfaces 548 and 550 thereof. The illustrated radial bead interlocking form 524 is, in some ways, a double sided variation of the rounded axial bead interlocking form of an earlier embodiment.

Figure 55:
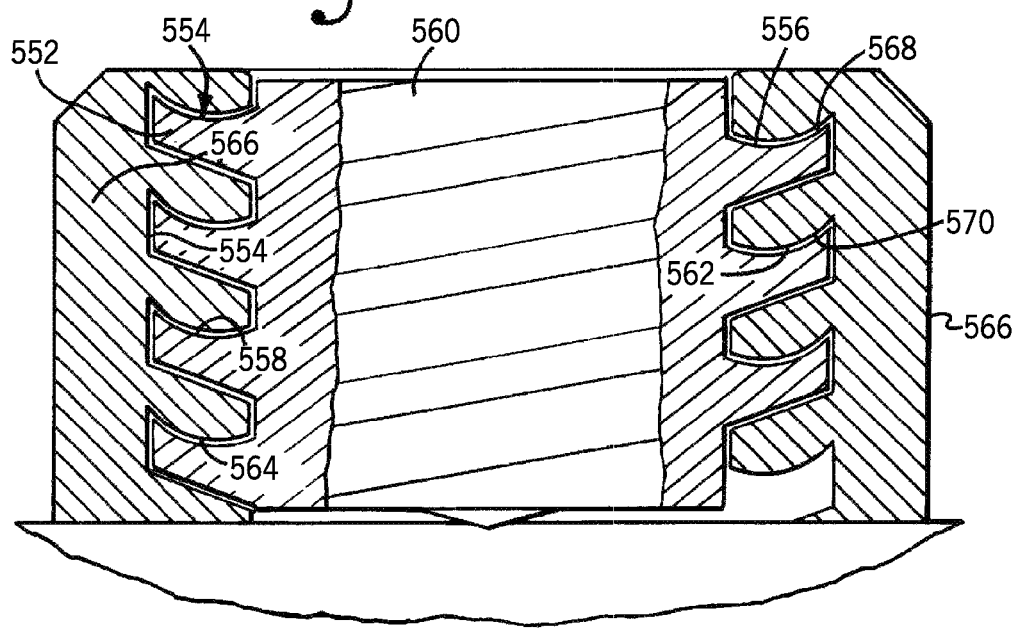
FIG. 55 is a view similar to FIG. 49 and illustrates details of a sixth modified bone screw and closure showing a scalloped depression or scooped embodiment of an interlocking form of the present invention.

FIGS. 55 and 56 illustrate a scalloped or scooped embodiment structure 572 including a pair of compound interlocking forms 552 and 554 according to the present invention. The interlocking form 552 is scalloped and, in effect, an inversion of the shallow rounded bead interlocking form similar to that of an earlier embodiment. The interlocking form 554 includes a shallow groove 556 formed in a thrust surface 558 of the external interlocking form 552 of a base 560 and a shallow bead 562 formed on a thrust surface 564 of the interlocking form 554 of a screw head 566. The groove 556 has a splay resisting surface 568 which cooperates with a complementary splay resisting surface 570 of the bead 562.

Illustrated in FIG. 57 is another guide and advancement structure 600 associated with a receiver member 601 and a closure member, such as a plug, 602 that is rotated into the receiver member 601. The structure 200 includes a first interlocking form 605 and a second interlocking form 606 attached to the closure member 602 and receiver member 601 respectively.

The first interlocking form 605 includes an arcuate upper surface 607 with a gripping or locking section 608. The second interlocking form 606 includes an arcuate lower surface 609 with a gripping or locking section 610. The interlocking forms 605 and 606 also have respective lower or leading surfaces 614 and 615 respectively that are sufficiently spaced to allow rotation about the axis thereof, but sufficiently close to be snug and not allow substantial movement of the forms 605 and 606 relative to each other in an axial direction without rotation.

FIG. 58 shows an alternative flange shaped embodiment of a guide and advancement structure 630 in accordance with the invention. The structure 630 is mounted on a closure 631 and a receiver 632 so that interlocking forms 633 and 634, which are seen in cross section, are helically mounted on the closure 631 and receiver 632 respectively.

The first interlocking form 633 is L or flange-shaped in cross section with a vertically or axially extending foot portion 640 with a gripping surface 641. The second interlocking form 634 generally complements the first and is also L or flange shaped except that a foot 643 thereof is much wider than the foot portion 640. The foot 643 has a gripping or wraparound surface 645 that abuts the surface 641 during assembly and resist radial movement between the receiver 632 and the closure 631.

Shown in FIG. 59 is another embodiment of a guide and advancement structure 660 in accordance with the invention. The structure 660 is utilized with a receiver 661 and a closure or plug 662. The structure 660 has first and second interlocking forms 663 and 664. The first interlocking form has an elongate wall 668 with a circular bead 669 attached to an end thereof opposite the closure 662. The bead 669 has opposed gripping surfaces 670 and 671. The second interlocking form 664 is shaped to mate with and generally surround the first interlocking form 663 except sufficient clearance is provided to allow the closure 662 to be rotated and advanced into the receiver 663 by sliding tangentially, but not radially. The second interlocking form 664 has a circular cross section channel 672 that receives the bead 669 and a pair of gripping surfaces 673 and 674 that engage and abut against the bead surfaces 670 and 671.

It is foreseen in accordance with the invention that certain regions of the interlocking forms may be eased or removed to allow for easier use which still maintaining the primary objective of resisting radial movement between the closure plug and the opposed arms of the bone screw to prevent splaying of such arms.

It is also seen in accordance with the invention that the axial aligned extension or depression on the described interlocking forms could in some cases be multiple in nature or formed by an undulating pattern.

Turning back to FIGS. 46-48, the helically wound guide and advancement structures 64 and 114 in the respective guide tools 9 and 10 are sized and shaped to receive the mating guide and advancement structure 181 of the closure top 62 and align with the guide and advancement structure 183 of the bone screw 4 to form a generally continuous helically wound pathway, but does not require locking between the closure top 62 and the tools 9 and 10, even when an interlocking flange form is utilized on the closure top 62.

Figure 42:
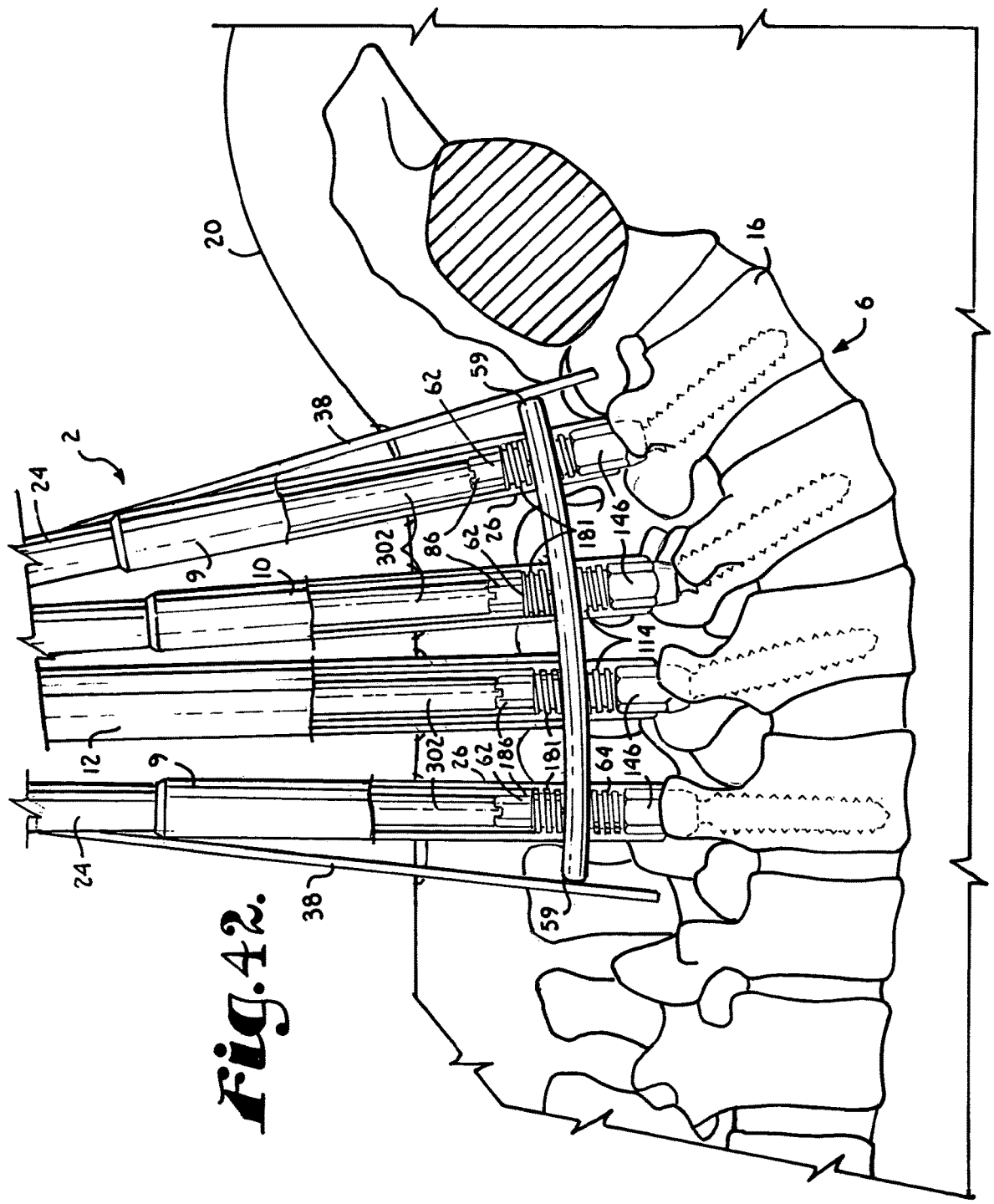
FIG. 42 is a partial and generally schematic view of a patient's spine similar to FIG. 40, showing cut-away portions of all four tool assemblies, illustrating an intermediate stage of implanting a rod.

The guides 64 and 114 allow the closure top 62 to be rotated and the surgeon to develop mechanical advantage to urge or drive the rod 8, while still outside or partially outside the bone screw 4, toward and into the bone screw head 146. This is especially helpful where the rod 8 is bent relative to the location of the vertebra 16 (which is sometimes the case) to which the rod 8 is to attach and is not easily placed in the bone screw head 146 without force and the mechanical advantage provided by the guides 64 and 114. In particular, the guide and advancement structures 64 and 114 on the respective tools 9 and 10 are located and positioned to align with the guide and advancement structure 183 on the insides of the bone screw arms 150 and 151, as shown in FIG. 42 and pass the closure top 62 therebetween while allowing the closure top 62 to continue to rotate and to continuously apply force to the rod 8, so as to aid in seating the rod 8 in the bone screw head 146.

Each closure top 62 also preferably includes a break-off head 186 that breaks from the cylindrical body 180 in a break-off region 187 upon the application of a preselected torque, such as 95 to 120 inch-pounds. The break-off head 186 preferably has a hexagonal cross section faceted exterior that is configured to mate with a similarly shaped socket of a final closure driving or torquing tool 190 described below. It is foreseen that different driving heads or other methods of driving the closure top 62 can be utilized with certain embodiments of the invention, such as non-break-off closure top designs.

Turning to FIGS. 60-62, another example closure member 600 is illustrated. The closure member 600 includes a plug, base section or base 602 and a break off head section 604 that breaks from the base 602 at a preselected torque. It is foreseen that such a closure could be made without a breakoff head and other structure could be added for torquing or removing the base section. Furthermore, it is foreseen that such a base both captures the rod and locks the rod as in the embodiment illustrated in FIGS. 60 to 62 or, alternatively, that the base could just capture the rod and a set screw could be used in a threaded bore in the base to lock the rod in place. The base section 602 is provided with the external interlocking form 402, as described above, which is compatible with the internal interlocking form 404 of the bone screw head 606. Both interlocking forms 402 and 404 are helically wound and rotatably rateable together through rotation or turning of the closure member 600 about the central axis 412 thereof. The head 608 includes structure for positive engagement by an installation tool (not shown) to install the closure member 600 in the bone screw member 610. The structure that allows for installation of the illustrated break off head 604 includes faces 612 forming a hexagonal shape or "hex" head to receive a complementary hexagonally shaped installation driver or tool. The head 604 also includes a central bore 614 and a cross bore slot 616. The outer end of the head 604 is chamfered at 618, and the bore 614 is provided with an interior conical countersink at 620. The region where the head 604 meets the base 602 is reduced in cross sectional thickness to form a weakened breakaway or fracture region 622. The breakaway region 622 is designed so that the head 604 separates from the base 602 when a selected torque is applied by the installation tool, as is diagrammatically illustrated by breaking away of the head 604 in FIG. 62. The base 602 is preferably provided with structure to facilitate removal of the base 602 from the implant head 606, such as the illustrated removal bores 624. The bores 624 may be formed by drilling from a lower end surface 626 of the plug 602, since an upper end surface 628 of the plug 602 is normally not accessible for drilling the bores 624 prior to break-off of the head 604. It is foreseen that many different types of removal devices or structures can be utilized with the base such as: axially aligned bores with hex, torx or other multifaceted cross-section, step down bores for engagement by an easy out, bores at the periphery or non axially aligned on the face of the base, bores with a left handed thread or the like. Further, the same structure used to torque the base on installation may be used to remove the base.

The base 602 is rotated into the receiving member of the bone screw head 606 to clamp the fixation rod 608 therein for any of a variety of surgical purposes. In general, the rod 608 is used to fix the position of a bone or portion of a bone, such as a plurality of vertebrae. The rod 608 may be anchored relative to some vertebrae and, in turn, used to secure other vertebrae in desired positions or orientations or used to properly align a series of vertebrae. It is generally required that the union formed between the bone screw 610, closure 600 and the rod 608 be very tight or snug to avoid relative movement therebetween. The fixation system 630 preferably employs structure that positively engages and seats the head 606 and/or the base 602 with respect to the rod 608, such as a conical set point 632 formed on the bottom surface 626 of the base 602 which engages the rod 608. The point 632 positively "bites" into the surface of the rod 608 to help prevent rotational or axial movement of the rod 608 relative to the screw 610. Alternatively or in combination with a point 632, other structures may be used to positively engage the closure plug 602 with the rod 608, such as a sharp edged coaxial ring (not shown) having a V-shaped cross section formed on the lower surface 626 of the base 602 or point extending upwardly from the channel.

The present invention is not intended to be restricted to a particular type of bone screw or bone screw closure mechanism. In the present embodiment, a polyaxial type bone screw 4 is utilized wherein the shank 148 is locked in position by direct contact with the rod 8. It is foreseen that the tool set 2 of the present invention can be used with virtually any type of bone screw, including fixed monoaxial and polyaxial bone screws of many different types wherein the head is locked relative to the shank by structure other than in the manner described in the illustrated embodiment.

With reference to FIGS. 22-25, the multi-purpose installation tool 12 of the tool assembly 1 of the invention includes an upper translation nut 202 rotatably and free wheelingably attached to a lower guide tool stabilizer or support sleeve 204. The sleeve 204 has an inner substantially cylindrical surface 205 defining a substantially hollow passageway 206 sized and shaped to slidingly receive an end tool 9 or an intermediate tool 10 therein. Alternatively, is foreseen that the sleeve could have an inner and outer planar surface. The sleeve 204 is elongate and includes a receiving end 207, a substantially cylindrical outer body 208 and a translation nut attachment end portion 210 disposed opposite the receiving end 207. The receiving end 207 not only functions to receive the guide tool 9 or 10 into the sleeve 204, but also as a pressing block 218 for contacting the flexible flap or spring tang 38 and as a pressing end 207 for contacting the rod 8 and translating the rod 8 toward the bone screw head 146 when the multi-purpose installation tool 12 is installed on the guide tool 9 or 10, as will be discussed more fully below.

The cylindrical body 208 further defines a slotted U-shaped or C-shaped channel 212 that opens radially at an opening 213 and also opens at the receiving end 207 and extends substantially along a length of the body 208 to a location 214 spaced from the nut attachment end portion 210. The channel opening has a side-to-side width 216 sized to receive the back wall tang portion or flexible flap 38 of the end guide tool 9 therethrough, when aligned therewith. For example, with reference to FIG. 38, the multi-purpose installation tool 12 is shown partially removed from an end guide tool 9 and deploying the tang 38 after the bone screw has been inserted. Because of the substantial length of the channel 212 as defined by the location 214 and because of the channel width 216, the multi-purpose installation tool 12 can be removed, turned 180° and reattached to the end guide tool 9 thereby providing access through the channel opening 213 for protrusion of the back wall tang portion or flap 38 of the end guide tool 9. The flap 38 is thus not encumbered or restricted by the tool 12 during the rod pushing application and the flap 38 can be flexed outwardly by a rod 8 (not shown) or other forces, when the devices are assembled in this configuration.

Disposed flush to the lower sleeve end 207 and rigidly attached to the inner cylindrical surface 205 is the solid guide tool alignment and tang/rod pressing block 218. The block 218 has a substantially smooth, planar and rectangular surface 220 facing inwardly radially from the inner surface 205. The block 218 also follows the curve of the cylindrical surface 220 at a surface 222 thereof. Thus, as shown in FIG. 24, the block 218 has a segment shape when observed from a bottom plan view. The term segment used herein is defined as the part of a circular area bounded by a chord and an arc of a circle cut off by the chord. This segment shape of the block 218 provides a mechanical advantage for compressing the flexible flap 38 flush with the end guide tool 9 and for advancing the rod 8 into the bone screw 4 with the multi-purpose installation tool 12 which will be discussed more fully below.

The flat, rectangular surface 220 provides structure for installing the guide tool 9 or 10 in a mating and desired alignment with respect to the multi-purpose installation tool 12. For example, with respect to the guide tool 10, a preferred alignment is that the rear wall 81 of the tool 10 be disposed adjacent to the surface 220 when inserting the tool 10 into the multi-purpose installation tool 12. Then, the tool 10 is slid into the multi-purpose tool sleeve 204, with the block 218 preventing axial rotation of the tool 10 with respect to the sleeve 204, and resulting in the preferred alignment of the opening 79 and the pass-through slot 11 of the tool 10 and the U-shaped channel 212 of the multi-purpose tool in this application.

With respect to the end guide tool 9, the block 218 with the planar surface 220 provides for the insertion of the tool 9 in a first, installation tang containing position or a second, rod pushing position. When utilizing the assembly 1 of the invention to install a bone screw 4, it is advantageous for the flexible back wall portion or tang 38 of the tool 9 to be fully restrained by the multi-purpose installation tool 12 and for the walls 68 and 69 to be locked in a non-splayable or anti-splay position. Therefore, in the first, bone screw installation tang containing position, the multi-purpose installation tool 12 is inserted onto the tool 9 with the back wall 28 of the tool 9 disposed adjacent to the sleeve surface 220. Then, the tool 9 and the sleeve 204 are attached with the block 218 preventing axial rotation of the tool 9 with respect to the multi-purpose installation tool 12. This results in the preferred alignment wherein the flexible back wall portion or tang 38 is disposed adjacent to the multi-purpose tool sleeve 204 and contained and disposed opposite the U-shaped channel 212. After the bone screw 4 is installed and it is desired to install the rod 8 in two or more bone screws 4, the multi-purpose installation tool 12 is removed from the end guide tool 9 and replaced thereon with the slot 44 and channel openings 40 and 94 adjacent to and facing the alignment block 218.

The translation nut 202 of the multi-purpose installation tool 12 is substantially cylindrical in shape and is shown with outer grooves 223 to aid a surgeon in handling the multi-purpose installation tool 12 and rotating the nut 202. The nut 202 further includes an inner cylindrical surface 224 defining an inner substantially cylindrical passage 226 communicating with the passage 206 of the sleeve 204. The inner surface 224 further includes a helical guide and advancement structure as shown by a V-shaped thread 228 that is configured to mate with the guide and advancement structure 50 of the end guide tool 9 or the guide and advancement structure 93 of the intermediate guide tool 10.

With reference to FIG. 25, the inner cylindrical surface 224 extends from an upper open end 230 of the translation nut 202 to an annular seating surface 232 extending radially outwardly and perpendicular to the cylindrical surface 224. As will be discussed more fully below, the surface 224 with associated thread 228 is of a length that provides an equivalent translation distance of the multi-purpose installation tool 12, and in particular the tang/rod pressing block 218, with respect to the guide tool 9 or 10 such that the pressing block 218 can be used to gradually push the rod 8 toward the bone screw 4 for the entire translation distance by rotating the nut 202 which can be continued until the rod is fully seated in the head of the bone screw.

Also with reference to FIG. 25, at the annular seating surface 232, the sleeve 204 is in sliding contact with the nut 202. A lower portion 234 of the nut 202 further defines a second inner cylindrical surface 236 of greater diameter than the surface 224. The surface 236 has a diameter slightly greater than a diameter of the sleeve 204 and is configured to slidingly receive the sleeve 204 into the nut 202 along the surface 236. The nut 202 further defines an annular recess or groove 238 configured to receive a pin 240 rigidly fixed to the sleeve 204. The pin 240 may be accessed for attachment and removal from the sleeve 204 through an aperture 242 disposed in the translation nut 202. The pin 240 slidingly mates with the nut 202 within the recess 238, keeping the nut 202 and sleeve 204 in an attached but freely rotatable relation.

With reference to FIGS. 26-28, the driver 14 of an assembly 1 according to the invention includes a handle 250, a guide tool fastener or nut 252, and an elongate cylindrical stem or shaft 254 having a lower cylindrical portion 255 integral with a bone screw engager shown as a socket 256. The socket 256 is configured to mate with the upper part of the bone screw shank 154. The shaft 254 with attached socket 256 is receivable in and passes through the interior of the guides 9 and 10, such as the channel 80 of the guide tool 10. The lower portion 255 has a slightly smaller diameter than a diameter of the remainder of the shaft 254, this smaller diameter provides for adequate clearance of the portion 254 from the guide and advancement structures 64 and 114 when the shaft 254 is installed within the interior of the respective guide tools 9 and 10. The stem or shaft 254 is rigidly attached to the handle 250 and coaxial therewith. Both the handle 250 and the guide tool fastener 252 include outer grooves 258 and 259 respectively, about outer cylindrical surfaces thereof to aid in gripping and rotating the respective components.

The guide tool fastener 252 is a substantially hollow cylinder disposed in coaxial relationship with the handle 250 and the shaft 254. The fastener has a threaded inner cylindrical surface 262 disposed at a lower portion 263 thereof, the threaded surface 262 configured to mate with the guide and advancement structure 50 of the end guide tool 9 or the guide and advancement structure 93 of the intermediate guide tool 10. The fastener 252 is disposed on the driver 14 between an annular surface 264 of the handle 250 and the pin 46 that is fixed to the shaft 254 and extends laterally therefrom.

The driver 12 further includes a lateral pin 266 projecting radially outwardly from a cylindrical surface 268 adjacent the handle 250. In the embodiment shown, the cylindrical surface 268 is integral with the handle 250 and fixedly attached to the shaft 254. The pin 266 is disposed within an annular recess 270 defined by the cylindrical surface 268, and surfaces of the fastener 252, including an upper seating surface 272, a lower seating surface 274 and an inner cylindrical surface 276. The pin 266 disposed in the recess 270 allows for both rotational and axial or vertical translational movements of the fastener 252 with respect to the shaft 254. Thus, as shown in FIG. 26, the fastener 252 is rotatable about an axis C. Furthermore, the fastener is slidable along the axis C between the annular surface 264 and the pin 46, with FIG. 26 showing a first or unattached position with the fastener 252 in contact with the annular surface 264 and FIGS. 27 and 28 showing a second, engagement position, with the fastener 252 partially covering, but not contacting the pin 46, with the pin 266 abutting the upper seating surface 272 prohibiting further downward or vertical (axial) translational movement of the fastener 252 with respect to the shaft 254.

As stated previously herein, the pin 46 is configured for sliding engagement with both the slot 44 of the guide tool 9 and the slot 88 of the guide tool 10 when the driver shaft 254 is disposed in an interior of the guide tool 9 or 10. When the pin 46 is received in the slot 44 or the slot 88, any relative rotational movement between the guide tool 9 or 10 and the driver 14 is prevented, but the driver is free to slide axially with respect to the guide tool 9 or 10. When the fastener or nut 252 is slid into the second position shown in FIGS. 27 and 28 and the fastener is mated with the guide and advancement structure 50 of the end guide tool 9 or the guide and advancement structure 93 of the intermediate guide tool 10 by rotating the fastener 252 to a location adjacent to the pin 46, with the pin 266 in contact with the upper seating surface 272, relative axial movement between the driver 14 and the guide tool 9 or 10 is also prevented.

With reference to FIGS. 1 and 29-35, a three-component assembly 1 according to the invention including the guide tool 9, the multi-purpose installation tool 12 and the driver 14 may be assembled as follows: The guide tool 9 shown with attached bone screw 4 is inserted into the multi-purpose installation tool 12 with the upper end 43 being inserted into the receiving end 207 of the multi-purpose installation tool 12. With respect to the assembly shown in FIGS. 29-31, illustrated is a particular assembly wherein the multi-purpose installation tool 12 is being utilized as a support or stabilizer for the end guide tool 9 during installation of the bone screw 4 into the vertebra 16, specifically, to contain and compress the tang 38 and to provide extra support to the walls, such as walls 68 and 69 of tool 9. Thus, the guide tool 9 is received into the multi-purpose installation tool 12 with the rear wall 28 facing the alignment block 218 as shown in FIG. 29.

As the guide tool 9 is received into the multi-purpose installation tool 12, rotational movement is prevented by the alignment block 218 in sliding contact with the flat surfaces 28 of the guide tool 9. The translation nut 202 is then rotated clock-wise as viewed from the top end 230 and shown by the arrow X, with the thread 50 of the guide tool 9 mating with the thread 228 disposed on the inner surface 224 of the translation nut 202. The translation nut 202 is preferably rotated until the upper end 43 of the guide tool 9 is positioned outside of the body of the nut 202 with a few of the threads 50 exposed as shown in FIGS. 30 and 31. Furthermore, the sleeve 204 cannot be translated beyond the pin 67 that stops the sleeve near the rod abutment recess 61 disposed near the end of the guide tool 9. During rotation of the translation nut 202, the guide tool 9 is held in a preferred bone screw installation position and any rotational movement of the tool 9 is prevented by the alignment block 218 in contact with the co-planar back walls or facets 71 of the guide tool 9 as well as the planar back surface of the tang 38. As illustrated in FIGS. 30 and 31, when the guide tool 9 is fully installed in the multi-purpose installation tool 12 in this first or bone screw installation position, the flexible back wall portion or flap 38 is compressed and retained in place between the side walls 32 and 33 by the alignment block 218.

Figure 38:
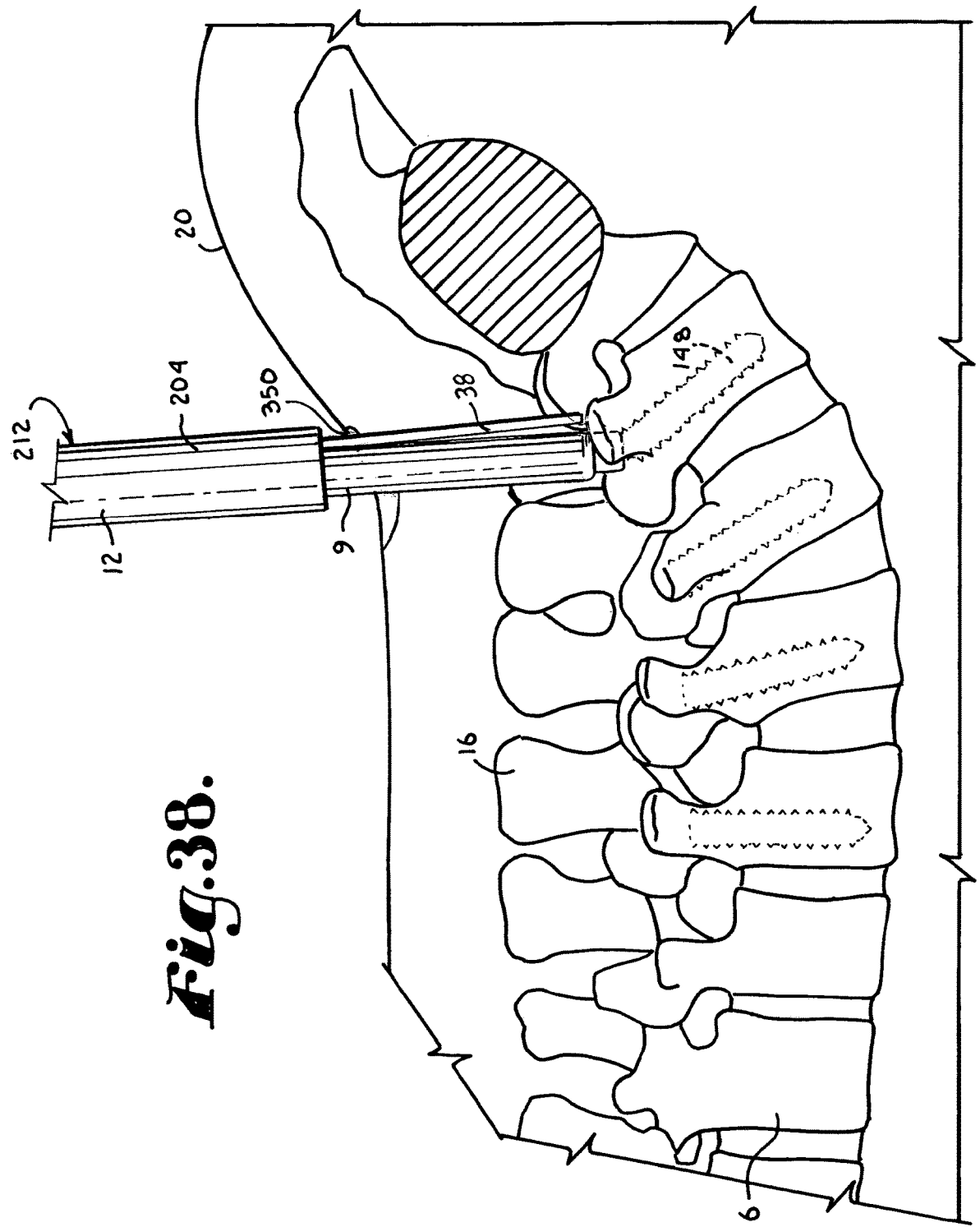
FIG. 38 is a partial and generally schematic view of a patient's spine, showing an end guide tool and the multi-purpose tool of the present invention being positioned for use in a process according to the invention.
Figure 41:
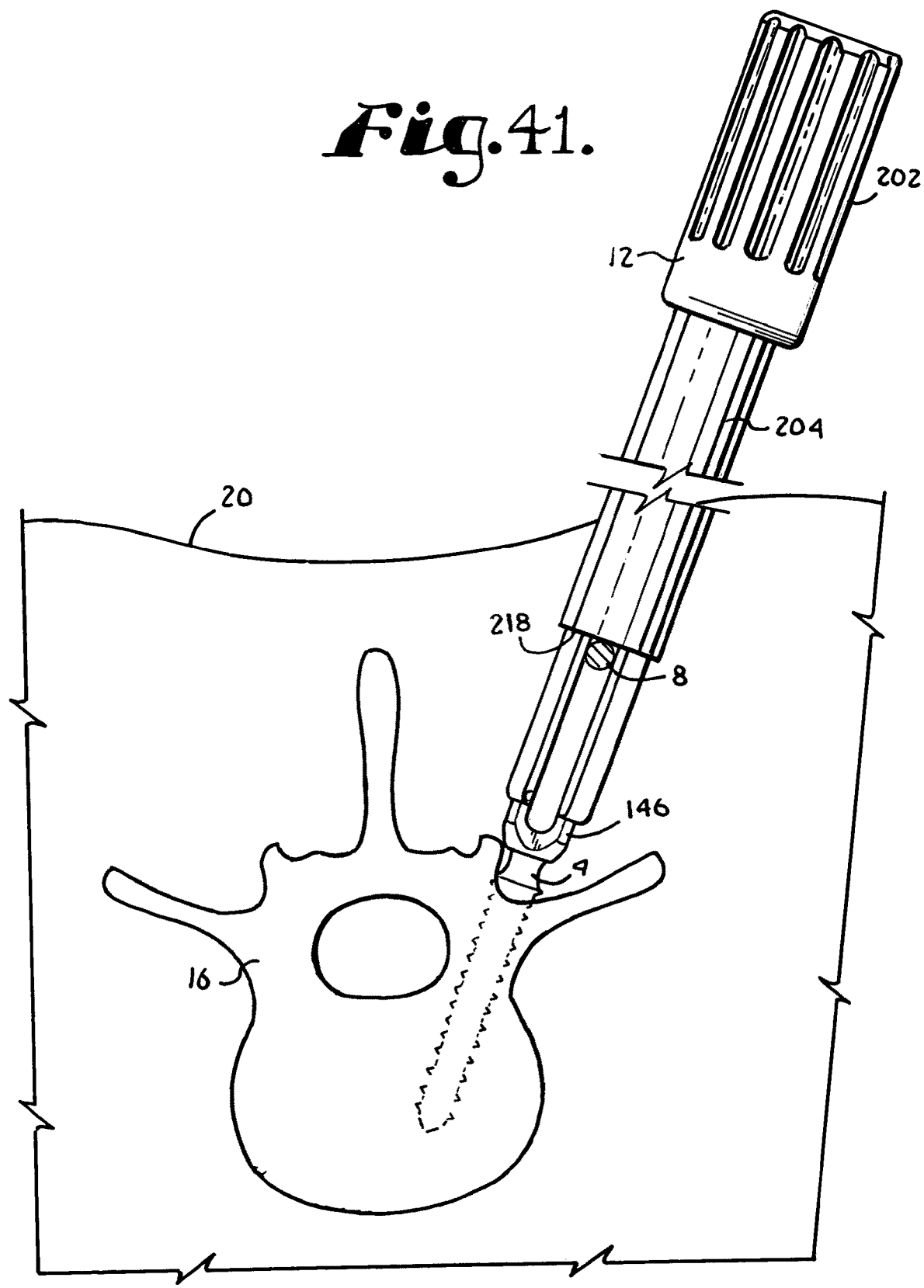
FIG. 41 is a partial and generally schematic cross-sectional view of the spine, taken along the line 41-41 of FIG. 40, showing an early stage of implanting a rod according to a process of the invention.

When the multi-purpose installation tool 12 is used as a rod pusher with the guide tool 9 as shown in FIGS. 38 and 41, the multi-purpose installation tool 12 is preferably used first as an end guide tool stabilizer and tang 38 container, as already described herein, and thus must first be removed by rotating the translation nut 202 counter-clockwise until the multi-purpose installation tool 12 is disengaged from the end tool guide 9 thereby deploying the tang 38. Thereafter, the multi-purpose installation tool 12 is removed and replaced on the guide tool 9 with the slot 44 and channel openings 40 and 94 adjacent to and facing the alignment block 218. As the multi-purpose installation tool 12 reinserted onto the guide tool 9, rotational movement is prevented by the alignment block 218 in sliding contact with the flat surfaces 47 and 48 of the guide tool 9. The translation nut 202 is then rotated clock-wise as shown by the arrow X (FIG. 29), with the thread 50 of the guide tool 9 mating with the thread 228 disposed on the inner surface 224 of the translation nut 202. Similar to what is shown in FIGS. 30 and 31, the translation nut 202 is rotated clockwise as shown by the arrow X, until the upper end 43 of the guide tool 9 is positioned outside of the body of the nut 202 with some of the threads 50 exposed. During rotation of the translation nut 202, the guide tool 9 is held in position and any rotational movement of the tool 9 is prevented by the alignment block 218 in contact with the co-planar front walls or facets 70 of the guide tool 9. When the multi-purpose installation tool 12 is used in this second or rod pushing position, the flexible back wall tang portion or flap 38 is not obstructed by the sleeve 204 of the multi-purpose installation tool 12 and may spring out or be further pushed out through the opening 213 of the U-shaped channel 212.

An assembly 1 according to the invention may also include the intermediate guide tool 10 in the place of the guide tool 9 as shown in FIGS. 40-42. Because the intermediate guide tool 10 includes a pass-through slot 111 rather than a flexible back wall tang portion 38, the alignment between the multi-purpose installation tool 12 and the guide tool 10 may be the same during bone screw installation as for the pushing of the rod 8. Therefore, the tool guide 10 may be inserted into the multi-purpose installation tool 12 with either the rear wall 81 or the slot 88 adjacent to and facing the alignment block 218.

Similar to the discussion herein with respect to the guide tool 9, as the guide tool 10 is inserted into the multi-purpose installation tool 12, rotational movement is prohibited by the alignment block 218 in sliding contact with either the rear wall 81 or the coplanar surfaces 91 and 92 of the guide tool 10. The translation nut 202 is then rotated clock-wise as viewed looking toward the top 87 of the tool 10, with the thread 93 of the guide tool 10 mating with the thread 228 disposed on the inner surface 224 of the translation nut. Similar to what is shown in FIGS. 30 and 31, the translation nut 202 is rotated until the upper end 87 of the guide tool 10 is positioned outside of the body of the nut 202 with some of the threads 93 exposed. During rotation of the translation nut 202, the guide tool 10 is held in position, with rotational movement of the tool 10 being prevented by the alignment block 218 in contact with the co-planar front walls or facets 109 or the co-planar rear walls or facets 110 of the guide tool 10.

Further discussion of the assembly 1 in this application will be directed toward the end guide tool 9 shown in the drawings. Unless specifically stated otherwise, the intermediate guide tool 10 can be utilized in similar fashion to what is being described herein with respect to the end guide tool 9.

With reference to FIGS. 1 and 32-35, after installation of the multi-purpose installation tool 12 to the guide tool 9, the driver 14 is inserted into the guide tool 9/multi-purpose installation tool 12 combination by inserting the socket end 256 into the end 43 of the guide tool 9 and sliding the shaft 254 into the interior of the guide tool 9 until the socket end 256 contacts and surrounds the upper part of the shank 154 of the bone screw 4 as shown in FIG. 35. As the shaft 254 is being inserted into the guide tool 9, the pin 46 on the shaft 254 of the driver 14 is aligned with and slid into the slot 44 of the guide tool 9. In order to more easily view the pin alignment process, the guide tool fastener 252 is placed in the first or unattached position with the fastener 252 in contact with the annular surface 264 as shown in FIG. 32. Also as shown in FIG. 32, preferably, the pin 46 is slid to a position disposed substantially within the slot 44 when the socket end 256 engages the shank 154 of the bone screw 4. The guide tool fastener or nut 252 is then rotated clockwise as viewed from the handle and illustrated by the arrow Y in FIG. 33, from the first unattached position toward the second engaged position, mating the thread 50 located near the end 43 of the guide tool 9 with the inner threaded surface 262 of the nut 252 of the driver 14. If, after the fastener 252 is rotated to a hand-tightened position, and a gap or space remains between the fastener 252 and the translation nut 202, as shown in FIG. 33, the translation nut 202 may then be rotated counter-clockwise as shown by an arrow Z in FIG. 33, and hand-tightened until the translation nut 202 abuts against the fastener 252, as shown in FIG. 34. The assembly 1 is then fully assembled and may be used to install the bone screw 4 into the vertebra 16 as will be described more fully below. Thereafter, the driver 14 may be removed by rotating the fastener 252 in a counter-clockwise direction (arrow Z) and sliding the shaft 254 out of the multi-purpose installation tool 12 through the open end 230.

Figure 44:
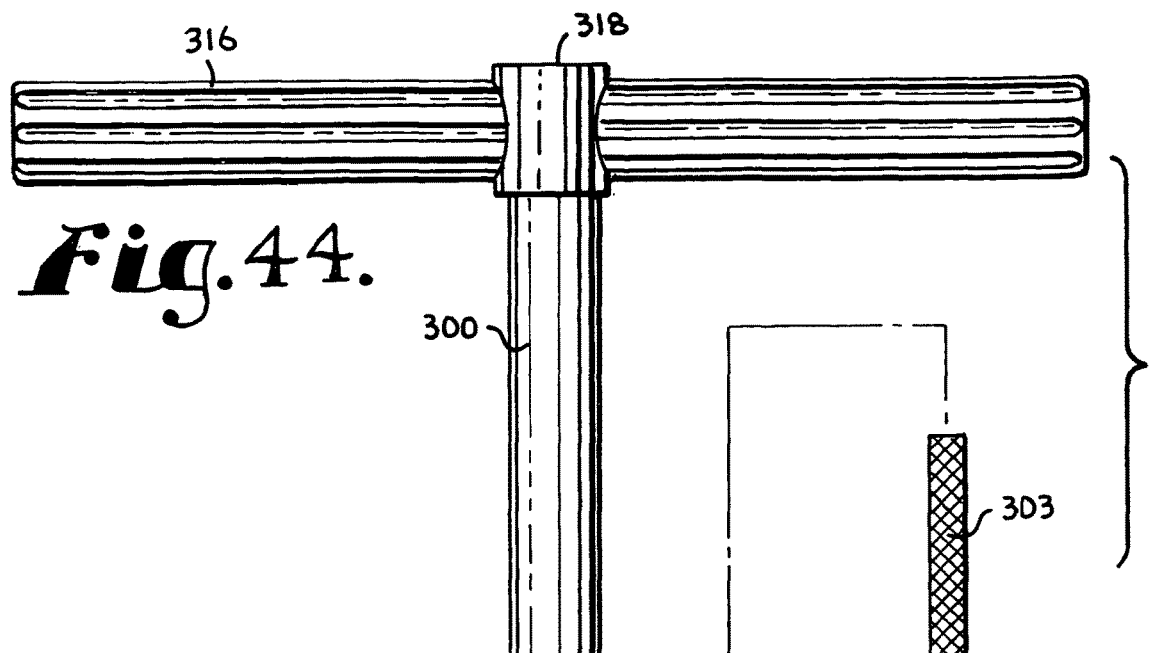
FIG. 44 is an exploded front elevational view of an anti-torque tool assembly according to the present invention showing an antitorque tool and a closure top installation tool cooperating with a break-away bone screw closure member.
Figure 45:
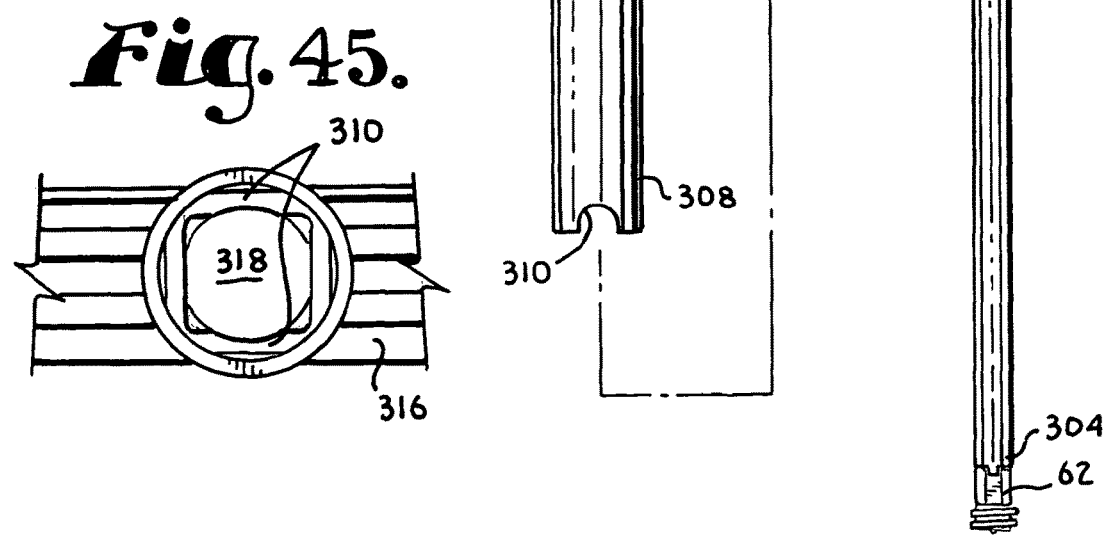
FIG. 45 is a bottom plan view of the anti-torque tool shown in FIG. 44.

Another tool used in implanting a spinal rod 8 is an antitorque tool 300 illustrated in FIGS. 44 and 45 and further shown in FIG. 44 with a closure top installation tool 302 engaging the break-away portion 186 of the closure top 62. The closure top installation tool 302 includes an upper handle portion 303 and a lower, closure top engagement portion 304 configured to mate with and rotate the closure top 62.

The antitorque tool 300 is also preferably used with a closure top torquing tool 305, shown in FIGS. 47 and 48. The tool 305 is used to torque and set the closure top 62, so it is snug against the rod 8, and thereafter break away the break-off head 186 in the manner shown in FIG. 48. The torquing tool 305 is preferably in the form of a socket as shown in the drawings to allow for adequate tightening of the closure top 62 and also ease in removal of the break-off head 186 as shown in FIG. 48.

The antitorque tool 300 includes a tubular hollow shaft 306 that is sized and shaped to be slidably received over the installation tool 302 and also the torquing tool 305. The shaft 306 has a lower end portion 308 that has a pair of diametrically spaced, curved bridges 310. Each of the bridges 310 is sized and shaped to fit over the rod 8, shown in FIGS. 47 and 48. When in place, as illustrated in FIG. 47, the antitorque tool 300 allows a surgeon to counter torque applied by the torquing tool 305, when applying torque to and breaking away the break-off head 186. The antitorque tool 300 also has an upper handle 316 disposed perpendicular to the shaft 306 and having an opening 318 through which the installation tool 302 and the torquing tool 305 passes in the manner suggested by FIGS. 46-48.

In use, the previously described tools are utilized to attach one or more rods 8 to the human spinal column 6. The procedure is begun by selection of a bone screw 4 in accordance with the size of the patient's vertebra 16 and the requirements of the spinal support needed. Bone screws 4 having a rotatable or polyaxial head 146 are preferred but not required for the procedure, as such allow relatively easy adjustment of the rod 8 in the tools 9 and 10 during placement and for movement of the tools 9 and 10, as described below. The bone screw 4 is also preferably cannulated so as to be receivable over and guided by a guide pin 355 as discussed more fully below.

A relatively small incision, such as an incision 350 in the skin 20 is then made for each bone screw 4 to be used. Preferably, the incisions are sized so as to snugly receive the tools of the invention. The incisions 350 are stretched into a round shape with a circumference equal to or just slightly larger than the multi-purpose installation tool 12. The skin 20 is relatively flexible and allows the surgeon to move the incision 350 around relative to the spine 6 to manipulate the various tools and implants, as required. In some cases, two screws can be inserted through one or the same incision.

Figure 36:
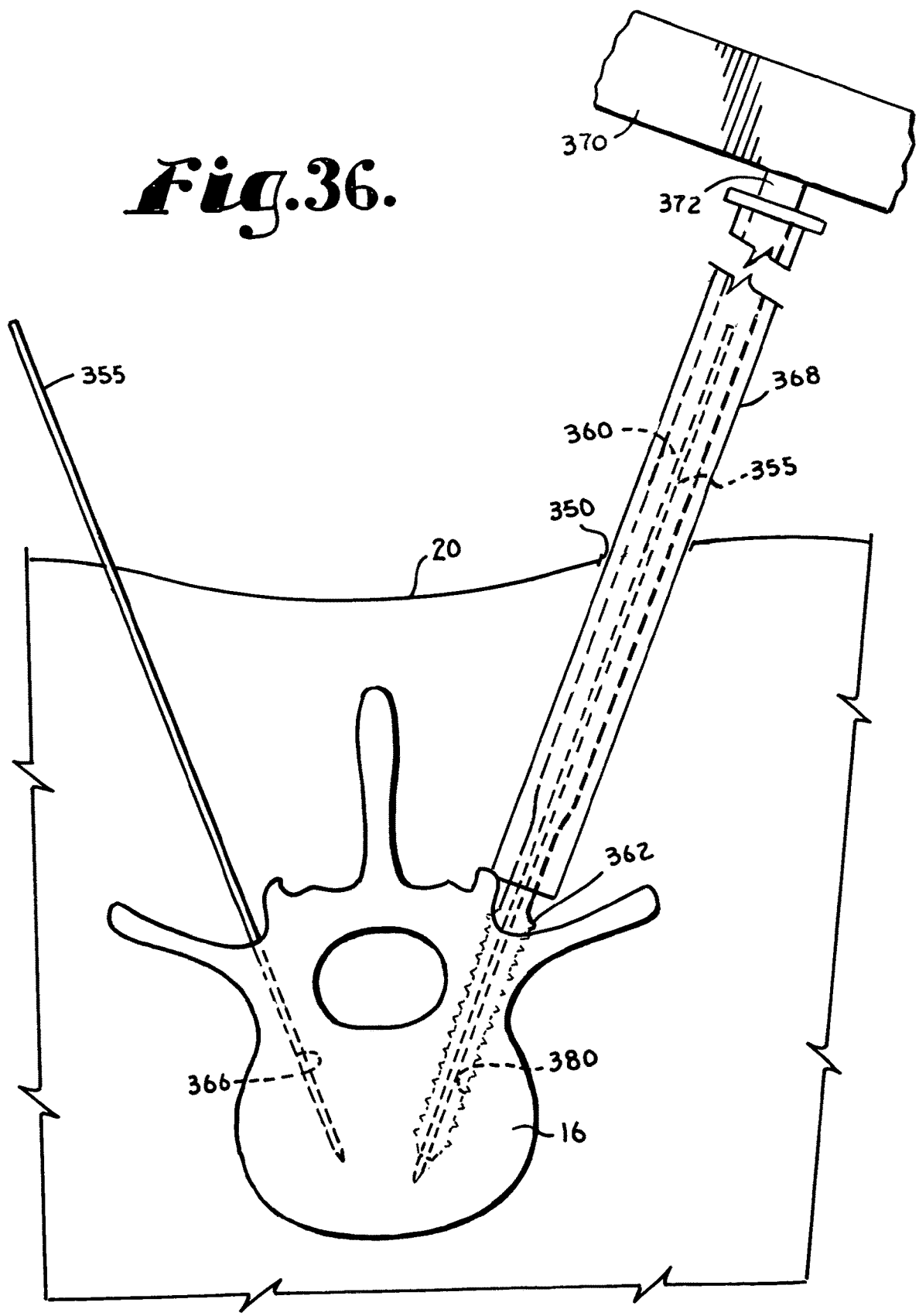
FIG. 36 is a partial and generally schematic cross-sectional view of a patient's spine, showing a thin guide pin installed at a first side thereof and a bone screw tap tool and threaded bore made thereby at a second side thereof.

With reference to FIG. 36, a drill (not shown) is utilized to form a first guide bore 366 in a vertebra 16 under guidance of non invasive imaging techniques, which procedure is well known and established. The thin pin or guide wire 355 is then inserted in the first guide bore 366. This first guide bore 366 and associated thin pin 355 function to minimize stressing the vertebra 16 and provide an eventual guide for the placement and angle of the bone screw shank 148 with respect to the vertebra 16.

The guide bore 366 is enlarged utilizing a cannulated drilling tool or tap 360 having an integral or otherwise attached cannulated and threaded bit 362 with an outer surface sized and shaped to correspond to the size and shape of the chosen threaded bone screw 4. The drilling tool 360 cooperates with a cylindrical holder or sleeve 368 having an inner surface in slidable mating arrangement with the tool 360 and being held in a position substantially co-axial therewith. The holder 368 is sized and shaped to fit within the incision 350 and prevents soft tissues from being rolled up in the threaded bit 362 as it is rotated. The tool 360 further includes a handle 370 fixedly attached to the tool 360 located at an end portion 372 thereof and of a size and shape for rotating the bit 362 along the pin 355 and into the first bore 366.

With the pin 355 still in place, the enlargement of the guide bore 366 begins by threading the thin pin 355 through the end of the tap and inserting the holder 368 into the incision until the holder comes into contact with the vertebra 16. The drill bit 362 is advanced downward along the pin 355 until the drill bit 362 comes into contact with the vertebra 16. The tool 360 is then rotated within the holder 368 using the handle 370, driving the bit 362 along the pin 355 until a full sized bore 380 is drilled to a depth desired by the surgeon. During drilling, the holder 368 remains stationary, shielding the surrounding tissue from the rotational movement of the bit 362 and tool 360.

The tool 360 is then removed by rotating the bit 362 in reverse until the bit 362 is outside the bore 380. The tool 360 is then removed from the holder 368, followed by the removal of the holder 368 through the incision 350.

Before placing the bone screw 4 in the vertebra 16, the bone screw 4 is preferably joined to an associated guide tool 9 or 10, an associated multi-purpose installation tool 12, and an associated driver 14. It is possible, but typically not desirable, to join a guide tool 9 or 10 to the bone screw 4 after the installation of the bone screw 4 to the vertebra 16. There also may be instances wherein it is desirable to join the bone screw 4 to an associated guide tool 9 or 10, but not to the multi-purpose installation tool support 12 or the driver 14 until after the bone screw 4 is installed in the vertebra 16, if at all. Furthermore, the driver 14 may be used with a guide tool 9 or 10 without the multi-purpose installation tool 12. However, it is preferable to utilize the multi-purpose installation tool 12 during installation of a bone screw 4 into the vertebra 16 as the tool 12 provides mechanical advantage and aids in preventing inadvertent splaying of side walls 32 and 33 of the end guide tool 9 and legs 102 and 103 of the intermediate guide tool 10.

The attachment structure 124 of the intermediate guide tool 10 is joined to a bone screw 4 by first rotating the tool 10 relative to the bone screw 4 so that the legs 102 and 103 are positioned as shown in FIGS. 17 and 18, with the facets 167 and 177 of the head 146 disposed between the guide tool legs 102 and 103, and with the facet 167 adjacent the leg 102 and the facet 177 adjacent the leg 103, thereby aligning the groove 158 with the large pin 126 and the groove 168 with the large pin 130. A slight splaying of the legs 102 and 103 is possible during alignment with the head arms 150 and 151.

The head 146 is then twisted into place by rotating the tool 10 axially in a clockwise direction as shown by the arrow T in FIGS. 18 and 19.

The twist-on procedure described herein with respect to the attachment structure 124 of the intermediate tool 10 is also followed with respect to the end guide tool 9 attachment structure 72. As previously stated herein, the attachment structure 72 is substantially similar to the attachment structure 124 of the intermediate tool 10, with the only difference being that the end guide tool 9 includes a flexible back wall tang portion 38 rather than the pass-through slot 111 of the intermediate guide tool 10.

After the bone screws 4 have been attached to the guide tools 9 and 10, a multi-purpose installation tool 12 is preferably attached to each of the guide tools 9 and 10. With respect to each of the intermediate guide tools 10, the multi-purpose installation tool 12 is preferably installed as follows: The rear wall 81 of the tool 10 is positioned adjacent to the surface 220 and the tool 10 is inserted into the hollow passage 206 and slid into the rod pusher sleeve 204 until the end 87 contacts the translation nut 210, with the block 218 preventing axial rotation of the guide tool 10 with respect to the multi-purpose installation tool 12, and resulting in the preferred alignment of the sleeve slot 11 and the opening 79 of the tool 10 with the U-shaped channel 212 of the multi-purpose installation tool 12. However, because the slot 11 is a pass-through slot, the alignment of the guide tool 10 with respect to the multi-purpose installation tool 12 is not critical to processes according to the invention. Therefore, in most instances the rear wall 81 of the tool 10 may also be positioned opposite the surface 220 upon entry into the multi-purpose installation tool 12.

The translation nut 202 is then rotated with the thread 228 of the nut 202 mating with the thread 93 of the tool 10. The nut 202 is rotated in a clockwise direction as illustrated by the arrow X in FIG. 29 until the end 87 is disposed outside of the nut 202 and positioned similar to what is shown with respect to the multi-purpose installation tool 12 and end guide tool 9 assembly shown in FIGS. 30 and 31. The abutment pin 118 prevents further rotation of the nut 202 and advancement of the sleeve 204 beyond the pin 118.

As shown in FIGS. 29-31, the end guide tools 9 are similarly equipped with multi-purpose installation tools 12. In order to compress the tang 38 during installation of a bone screw 4 into a vertebra 16, the tool 9 is received into the multi-purpose installation tool 12 with the back wall 28 of the tool 9 disposed adjacent to the surface 220. Then the multi-purpose installation tool 12 is slid onto the tool 9 until the end 43 contacts the translation nut 202, with the block 218 preventing axial rotation of the tool 9 with respect to the multi-purpose installation tool 12, and resulting in the preferred alignment wherein the flexible back wall tang portion or flap 38 is disposed adjacent to the guide tool sleeve 204 disposed opposite the U-shaped channel 212. The translation nut 202 is then rotated with the thread 228 of the nut 202 mating with the thread 50 of the end guide tool 9. The nut 202 is rotated in a clockwise direction as illustrated by the arrow X in FIG. 29 until the end 43 is disposed outside of the nut 202 and positioned as shown in FIGS. 30 and 31, but not beyond the pin 67.

The driver 14 is then installed into the guide tool 9 as shown in FIGS. 32-35 and as follows: The driver 14 is first prepared for ease of insertion by placing the guide tool fastener 252 in the first or unattached position with the fastener 252 in contact with the annular surface 264 of the driver 14 as shown in FIG. 32. Then, the driver end 256 is inserted into the guide tool 9 at the end 43 with the stem 254 being slid into the guide tool 9 with the pin 46 aligned with the channel 39 until coming to a stop with the pin 46 disposed in the slot 44 and the bone screw engager 256 in contact with the bone screw upper shank 154. A slight rotation or jiggling of the bone screw shank 148 may be required for the hex socket of the bone screw engager 256 to become positioned in operational engagement with the hex shaped upper shank 154. The guide tool fastener or nut 252 is then moved downward and toward the end 43 and then rotated clockwise as viewed from the handle 250 and illustrated by the arrow Y in FIG. 33, mating the thread 50 disposed near the end 43 of the guide tool 9 with the inner threaded surface 262 of the nut 252 of the driver 14. The nut 252 is rotated in this clock-wise fashion and hand-tightened until further translation of the nut 252 along the guide tool 9 is prevented by the pin 266 abutting the upper seating surface 272.

If, after the fastener 252 is rotated to a hand-tightened position, and a gap or space remains between the fastener 252 and the translation nut 202 as shown in FIG. 33, the translation nut 202 is rotated counter-clockwise as shown by the arrow Z in FIG. 33, and hand-tightened until the translation nut 202 abuts against the fastener 252 as shown in FIG. 34. The assembly 1 is now ready for bone screw installation into the vertebra 16.

The driver 14 is installed into the intermediate guide tool 10 and multi-purpose installation tool 12 assembly in steps similar to that described above with respect to the end guide tool 9.

A series of bone screws 4 are installed in each vertebra 16 to be attached to the rod 8 by inserting each of the assemblies 1 through the skin incision 350 as shown in FIG. 37. The screw 4 is then rotated and driven into the tapped bore 380 with the surgeon holding and rotating the assembly 1 with the driver handle 250, thereby rotating the entire assembly 1 as one unit until the shank 148 is disposed at a desired depth in the tapped bore 380 of the respective vertebra 16. Preferably, the shank 148 is also cannulated to receive the pin 355, providing additional guidance for installation of the bone screw 4 into the vertebra 16.

After a specific bone screw 4 is installed, the driver 14 is removed from either the guide tool 9 or 10 by rotating the fastener 252 in a counter-clockwise direction (illustrated by the arrow Z in FIG. 33) and sliding the shaft 254 towards the open end 230 of the multi-purpose installation tool 12 and pulling the driver 14 out of the assembly 1 by the handle 250.

With respect to the end guide tools 9, the multi-purpose installation tool 12 is then removed by rotating the translation nut 202 counter-clockwise until the thread 228 disposed on the inner surface 224 of the translation nut 202 is disengaged from the thread 50 of the tool 9. The multi-purpose installation tool 12 is then slid off of the tool 9 deploying the flexible flap 38, as shown in FIG. 38. If desired at this junction of a process according to the invention, the multi-purpose installation tool 12 many then be rotated 180 degrees and replaced on the tool 9 with the slot 44 and the channel openings 40 and 94 aligned adjacent to and facing the alignment block 218 of the multi-purpose installation tool 12 for a rod pushing application. The translation nut 202 is then rotated clockwise as illustrated by the arrow X in FIG. 29. In this rod pushing position, the flexible tang 38 is extendible into the U-shaped channel 212 of the multi-purpose installation tool 12.

Figure 39:
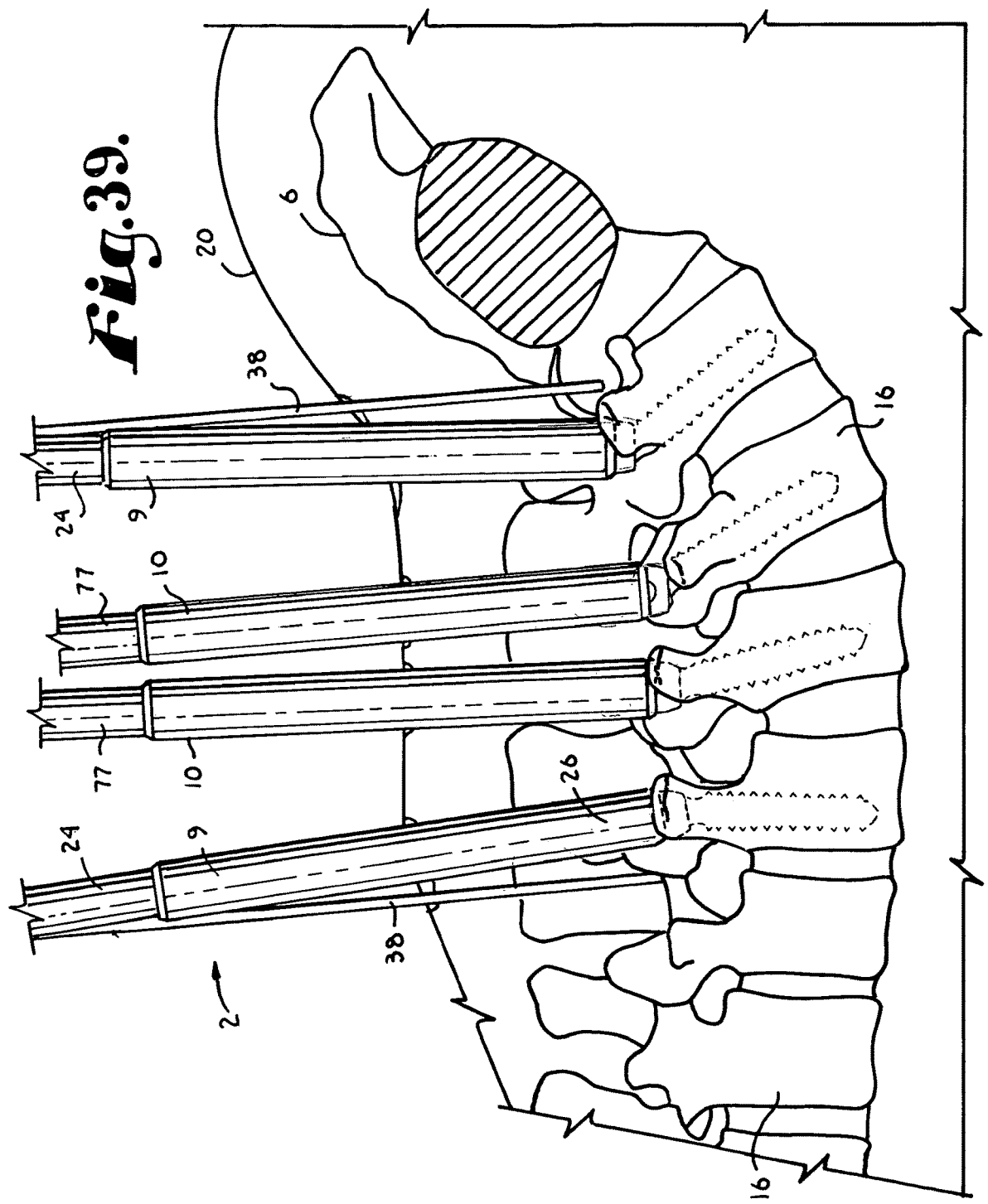
FIG. 39 is a partial and generally schematic view of a patient's spine, showing a pair of end tools and a pair of intermediate tools of the present invention being positioned for use in a process according to the invention.

For each bone screw 4, an associated guide tool 9 or 10 extends through the skin 14, as illustrated in FIG. 39. An end guide tool 9 is located at each end of the series of bone screws 4 and an intermediate guide tool 10 is located on each intermediate bone screw 4.

In order to install a rod 8 in two or more bone screws 4, it may not be necessary to equip each guide tool 9 or 10 with a multi-purpose installation tool 12. For example, with reference to FIG. 40, for a particular procedure, it may be desirable to utilize only one multi-purpose installation tool 12 with a tool set 2 according to the invention. In the process illustrated by the FIG. 40, the multi-purpose installation tools 12 have been removed from both of the end guide tools 9 and both of the intermediate guide tools 10 after which a rod 8 has been inserted and a multi-purpose tool 12 reattached to one tool 10. Some pushing of the rod may be accomplished by just extending a rod or tool down the central channel of the guide tools 9 and 10 when mechanical advantage is not required to move the rod 8. As required by the surgeon, one or more multi-purpose installation tools 12 may be added or removed at any time during the course of the rod pushing or reducing procedure.

With reference to FIG. 39, prior to installation of the rod 8, the end guide tools 9 are turned or rotated so the channels 55 therein face one another and the intermediate guide tools 10 are aligned so the pass-through slots 111 align with the channels 55.

With reference to FIG. 40, the rod 8 has been inserted diagonally through one of the end skin incisions 350 with the adjacent end guide 9 pushed to the side, so that one of the rod ends 59 first passes through the slots 111 in the intermediate guide tools 10 and then into the channel 55 of one of the guide tools 9. Back muscle tissue separates easily here to allow the upper insertion of the rod 8 and can be further separated by finger separation or cutting through one of the incisions 350, if required.

After initial insertion, the remaining opposed end 59 of the rod 8 is positioned in the channel 55 of the end guide tool 9 that is located next to the insertion point of the rod 8. Manipulation of the rod 8 in the channels 55 is aided by the back wall tang portions or flexible flaps 38 of the guide tools 9 which may also be moved like a joy-stick toward or away from each other by the surgeon. Furthermore, once the rod 8 is disposed within the channels 111 and 55, the back wall portions or flaps 38 resiliently bias against the rod ends 59, substantially holding and containing the rod 8 in place between the end guide tools 9 of the tool set 2. The reason that the tangs 38 are needed is that the rod 8 extends beyond the end bone screws 4 and the end guide tool 9 are located on the end bone screws 4. Also, the rod may tend to slip out of one end screw head. When the rod is spaced above the bone screws 4, the guide tools 9 can be manipulated to be spaced farther apart to receive the rod 8 therebetween, but as the rod 8 nears the bone screws 4, the guide tools 9 cannot be manipulated enough to compensate so the rod 8 must extend beyond the bodies of the guide tool 9. Therefore, the tangs 38 allow the rod 8 to be controlled and positioned outwardly of the end bone screws 8. Moreover, the position of the rod 8 is controlled by equal pressure applied by the tangs 38 so that the rod 8 extends past the bone screws 4 approximately an equal amount on each side.

Also with reference to FIGS. 40 and 41, once the rod 8 is positioned in the guide tools 9 and 10, the multi-purpose installation tool 12 may be utilized to push the rod 8 toward the bone screw 4, normally when mechanical advantage is needed to seat the rod 8 in the bone screws 4. This is accomplished by rotating the translation nut 202 in a clockwise direction (as viewed from above the skin 20), thereby translating the sleeve 204 in a downward direction toward the bone screw 4, with the guide tool alignment block 218 abutting and pushing against the rod 8.

As shown in FIG. 40, it may also be desirable to simultaneously or thereafter push the rod 8 toward the screw 4 of one or more guide tools 9 and 10 utilizing the closure top installation tool 302 pushing against a closure top 62 that in turn pushes against the rod 8. In particular, a closure top 62 is placed in the elongate top to bottom channel associated with the guide tools 9 and 10, preferably by entry from the side such as into the channel opening 40 of the guide tool 9 or alternatively into the channel 39 through the top end 43 of the guide tool 9. If the guide tool 9 or 10 has the multi-purpose installation tool 12 attached, the closure top 62 can be placed into the guide tool by side insertion into the U-shaped channel 212. The closure top installation tool 302 is then inserted into the top end 43 and through the channels disposed within the guide tool 9, until the engagement portion 304 mates with a cooperating aperture disposed in the break-off head 186. The closure top 62 is then driven or pushed under manual control of the surgeon by use of the installation tool 145 toward the rod 4.

With reference to FIG. 42, near the bottom of the guide tools 9 and 10, such as near the end 112 of the intermediate tool 10 and the bottom 36 of the back wall 28 of end guide tool 9, the closure top 62 engages the helically wound guide and advancement structures 64 and 114 of respective guide tools 9 and 10. The tools 302 and mated closure tops 62 are then rotated, mating the closure tops 62 with associated guide tools 9 and 10 so as to drive the closure top 62 downward against the rod 8 and to urge the rod 8 downward into the bone screw channel 153. Preferably, the translation nut 202 of the multi-purpose installation tool 12 is rotated in a clockwise direction, translating the sleeve 204 and block 218 downwardly slightly in advance or substantially concurrent with the advancement of the closure tops 62, providing additional mechanical advantage for the block flat surface 222 against the rod 8.

Figure 43:
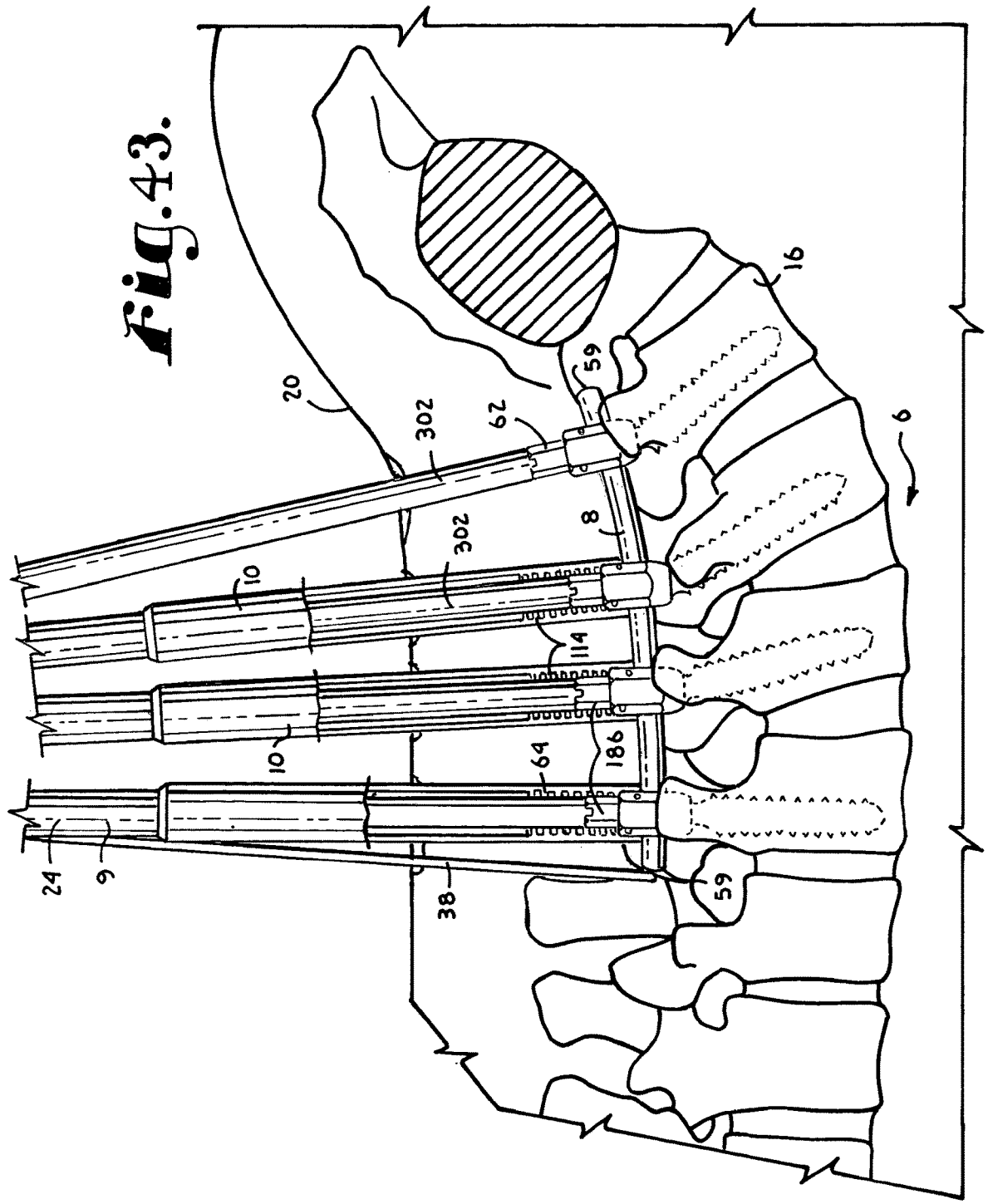
FIG. 43 is a partial and generally schematic view of a patient's spine similar to FIG. 42, showing cut-away portions of three of the tool assemblies and one assembly without an end tool, illustrating the rod fully installed in all the bone screws.

With reference to FIG. 43, at the bottom of the guide tool 9 or 10, the closure top mating structure 181 engages and begins to mate with the guide and advancement structure 183 on the respective bone screw 4 and continued rotation of the tool 302 drives the rod 8 downward and into engagement with the upper part of the bone screw shank 154, so as to snug against and frictionally lock the shank 148 in position relative to the bone screw head 146.

Once all of the closure tops 62 are in final seated position in respective bone screws 4 and the surgeon is satisfied with the position of all of the elements, such as is illustrated in FIG. 43, any and all multi-purpose installation tools 12 are removed by rotating the nut 202 counter-clockwise followed by sliding the sleeve 204 off of the guide tool 9 and 10 and out of the incision 350. Thereafter, each of the guide tools 9 and 10 are now removed by rotating each guide tools 9 and 10 ninety degrees so that the recesses 116 straddle the rod 8 to allow the attachment structure 72 or 124 to disengage from the receiver portion 145 on the bone screw 4. The guide tool 9 or 10 is then pulled axially upward away from the bone screw 4, along the tool 302 and then out of the incision 350.

The antitorque tool 300 is mounted over each closure top installation tool 302, utilizing the tool 302 as a guide for re-entry through the incision 350. The antitorque tool 300 is slid along the tool 302 until the bridges 310 straddle the rod 8, preventing axial rotation of the tool 300. As shown in FIG. 46, the closure top installation tool 302 is then pulled axially upward away from the bone screw 4 and out of the incision 350.

With reference to FIG. 47, the closure top torquing tool 305 is then inserted into the antitorque tool 300 and engaged with the break-off head 186. By cooperative use of the tools 300 and 305 a preselected torque is manually applied to the break-off head 186 which breaks from the closure top 62 as illustrated in FIG. 48 and is thereafter removed, followed by removal of the antitorque tool 300, after which the incision 165 is closed.

It is to be understood that while certain forms of the present invention have been illustrated and described herein, it is not to be limited to the specific forms or arrangement of parts described and shown. For example, it is foreseen that more than one tool could be used to provide the described functions for the multi-purpose installation tool 12.

What is claimed is:

1. A method for securing an elongate rod to a bone anchor, the method comprising:
   providing a receiver having a longitudinal axis, a base, and an upper portion defining a channel configured to receive the elongate rod, the channel extending between a front surface and an opposite back surface of the receiver and communicating with a top surface defining a top of the receiver, the receiver further comprising exterior side surfaces and interior surfaces opposite the exterior side surfaces, the interior surfaces including a helically wound thread form formed in at least a portion of the interior surfaces, the front surface includes a front planar surface, the back surface includes a back planar surface that is parallel to and opposite of the front planar surface, and the exterior side surfaces comprising first and second exterior side surfaces, the first exterior side surface including a first planar exterior side surface, the second exterior side surface including a second planar exterior side surface that is parallel to and opposite of the first planar exterior side surface;
   providing a closure configured to be positioned within the channel to secure the elongate rod to the receiver in a locked configuration, the closure comprising a cylindrical body having a central axis and an external surface with a mating continuous helically wound thread form having a thread pitch formed on at least a portion of the external surface, the helically wound thread form of the closure having a lower clearance surface extending perpendicular relative to the central axis, an outer cylindrical crest surface extending parallel relative to the central axis and an upper load surface extending perpendicular to the central axis of the cylindrical body of the closure, the closure further comprising a lower surface configured to engage the elongate rod positioned in the channel of the receiver; and
   positioning the closure within the channel of the receiver to secure the elongate rod to the receiver in the locked configuration,
   wherein, in the locked configuration, the closure does not extend over any part of the top surface defining the top of the receiver, and the entire lower clearance surface and the entire outer cylindrical crest surface of the helically wound thread form of the closure are spaced apart from the helically wound thread form of the receiver.

2. The method of claim 1, wherein the closure is a single piece structure.

3. The method of claim 2, wherein the closure includes a breakoff portion.

4. The method of claim 1, wherein the lower surface of the closure includes a protrusion centered along the central axis that is configured to engage the elongate rod positioned in the channel of the receiver.

5. The method of claim 1, wherein the first planar exterior side surface and the second planar exterior side surface are not recessed within the first exterior side surface and the second exterior side surface, respectively.

6. The method of claim 1, wherein the first exterior side surface and the second exterior side surface each include a horizontal radiused tool engaging groove (HRTEG) adjacent the top of the receiver that includes a downwardly-facing surface, an opposed upwardly-facing surface and an outward-facing surface between the downwardly-facing surface and the upwardly-facing surface, wherein the downwardly-facing surface, the upwardly-facing surface, and the outward-facing surface, for each of the HRTEG, extends continuously to at least one of the front planar surface on the front surface or the back planar surface on the back surface of the receiver.

7. A method for securing an elongate rod to a bone anchor, the method comprising:
   providing a receiver having a longitudinal axis, a base, and an upper portion defining a channel configured to receive the elongate rod, the channel extending between a front surface and an opposite back surface of the receiver and communicating with a top surface defining a top of the receiver, the receiver further comprising exterior side surfaces and interior surfaces opposite the exterior side surfaces, the interior surfaces including a helically wound thread form formed in at least a portion of the interior surfaces, the front surface includes a front planar surface, the back surface includes a back planar surface that is parallel to and opposite of the front planar surface, and the exterior side surfaces comprising first and second exterior side surfaces, the first exterior side surface including a first planar exterior side surface, the second exterior side surface including a second planar exterior side surface that is parallel to and opposite of the first planar exterior side surface;
   providing a closure configured to be positioned within the channel to secure the elongate rod to the receiver in a locked configuration, the closure comprising a cylindrical body having a central axis, a top and an external side surface with a mating continuous helically wound thread form having a thread pitch formed on at least a portion of the external side surface, the helically wound thread form of the closure having a lower clearance surface extending outwardly and upwardly toward the top of the closure at an angle relative to a perpendicular line to the central axis, an outer cylindrical crest surface extending parallel relative to the central axis and an upper load surface extending outwardly and upwardly toward the top of the closure at an angle relative to a perpendicular line to the central axis that is less than the angle for the lower clearance surface, the closure further comprising a lower surface extending continuously across a diameter thereof configured to engage the elongate rod positioned within the channel of the receiver; and
   positioning the closure within the channel of the receiver to secure the elongate rod to the receiver in the locked configuration,
   wherein, in the locked configuration, the closure does not extend over any part of the top surface defining the top of the receiver, and the entire lower clearance surface and the entire outer cylindrical crest surface of the helically wound thread form of the closure are spaced apart from the helically wound thread form of the receiver.

8. The method of claim 7, wherein the closure is a single piece structure.

9. The method of claim 8, wherein the closure includes a breakoff portion.

10. The method of claim 7, wherein the lower surface of the closure includes a protrusion centered along the central axis that is configured to engage the elongate rod positioned in the channel of the receiver.

11. The method of claim 7, wherein an outer portion of the upper load surface forms an acute angle with respect to the outer cylindrical crest surface.

12. The method of claim 7, wherein the first planar exterior side surface and the second planar exterior side surface are not recessed within the first exterior side surface and the second exterior side surface, respectively.

13. The method of claim 7, wherein the first exterior side surface and the second exterior side surface each include a horizontal radiused tool engaging groove (HRTEG) adjacent the top of the receiver that includes a downwardly-facing surface, an opposed upwardly-facing surface and an outward-facing surface between the downwardly-facing surface and the upwardly-facing surface, wherein the downwardly-facing surface, the upwardly-facing surface, and the outward-facing surface, for each of the HRTEG, extends continuously to at least one of the front planar surface on the front surface or the back planar surface on the back surface of the receiver.

\* \* \* \* \*